US011028387B2

(12) United States Patent
Yokota et al.

(10) Patent No.: US 11,028,387 B2
(45) Date of Patent: Jun. 8, 2021

(54) DOUBLE-STRANDED AGENTS FOR DELIVERING THERAPEUTIC OLIGONUCLEOTIDES

(71) Applicant: National University Corporation Tokyo Medical and Dental University, Tokyo (JP)

(72) Inventors: Takanori Yokota, Tokyo (JP); Kazutaka Nishina, Tokyo (JP); Kotaro Yoshioka, Tokyo (JP); Hidehiro Mizusawa, Tokyo (JP)

(73) Assignee: National University Corporation Tokyo Medical and Dental University, Tokyo (JP)

( * ) Notice: Subject to any disclaimer, the term of this patent is extended or adjusted under 35 U.S.C. 154(b) by 0 days.

(21) Appl. No.: 14/892,664

(22) PCT Filed: May 30, 2014

(86) PCT No.: PCT/JP2014/002882
§ 371 (c)(1),
(2) Date: Nov. 20, 2015

(87) PCT Pub. No.: WO2014/192310
PCT Pub. Date: Dec. 4, 2014

(65) Prior Publication Data
US 2016/0145614 A1      May 26, 2016

Related U.S. Application Data

(60) Provisional application No. 61/829,239, filed on May 30, 2013.

(51) Int. Cl.
*C12N 15/113* (2010.01)

(52) U.S. Cl.
CPC ...... *C12N 15/113* (2013.01); *C12N 2310/113* (2013.01); *C12N 2310/315* (2013.01); *C12N 2310/321* (2013.01); *C12N 2310/3231* (2013.01); *C12N 2310/341* (2013.01); *C12N 2310/3515* (2013.01)

(58) Field of Classification Search
CPC ... C12N 15/11; C12N 15/113; C12N 2310/11; C12N 2310/14; C12N 2320/33
See application file for complete search history.

(56) References Cited

U.S. PATENT DOCUMENTS

| | | | |
|---|---|---|---|
| 6,043,060 A | 3/2000 | Imanishi | |
| 2002/0068708 A1 | 6/2002 | Wengel et al. | |
| 2003/0105309 A1 | 6/2003 | Imanishi et al. | |
| 2006/0105975 A1 | 5/2006 | Pendergrast et al. | |
| 2007/0167387 A1 | 7/2007 | Imanishi et al. | |
| 2011/0003881 A1* | 1/2011 | Brown | A61K 31/713 514/44 A |
| 2014/0288158 A1* | 9/2014 | Rajeev | C12N 15/113 514/44 A |
| 2015/0011745 A1* | 1/2015 | Tachibana | C12N 15/113 536/24.5 |

FOREIGN PATENT DOCUMENTS

| | | |
|---|---|---|
| JP | 10-195098 A | 7/1998 |
| JP | 10-304889 A | 11/1998 |
| JP | 2002-521310 A | 7/2002 |
| JP | 2007-523601 A | 8/2007 |
| WO | WO 03/011887 A2 | 2/2003 |
| WO | WO 2004/069991 A1 | 8/2004 |
| WO | WO 2005/021570 A1 | 3/2005 |
| WO | WO 2005/111238 A2 | 11/2005 |
| WO | WO 2007/131238 A2 | 11/2007 |
| WO | WO 2007/143315 A2 | 12/2007 |
| WO | WO 2008/029619 A1 | 3/2008 |
| WO | WO 2008/043753 A2 | 4/2008 |

OTHER PUBLICATIONS

Chang et al., A structure-activity relationship study of siRNAs with structural variations, 2007, BBRC, vol. 359, pp. 997-1003.*
Pirollo et al., Materializing the potential of small interfering RNA via a tumor-targeting nanodelivery system, 2007, Cancer Research, vol. 67, pp. 2938-2943.*
Krützfeldt et al., Silencing of microRNAs in vivo with 'antagomirs', 2005, Nature, vol. 438, pp. 685-689.*
Lamberton et al., Varying the nucleic acid composition of siRNA molecules dramatically varies the duration and degree of gene silencing, Molecular Biotechnology, vol. 24, pp. 111-119. (Year: 2003).*

(Continued)

*Primary Examiner* — Dana H Shin
(74) *Attorney, Agent, or Firm* — Foley & Lardner LLP

(57) ABSTRACT

Disclosed are double-stranded nucleic acid agents that can deliver a therapeutic oligonucleotide within a biological sample, and methods for using the same. In one embodiment, the double-stranded nucleic acid agent comprises a first strand comprising a first RNA region, and a second strand comprising a first DNA region, wherein said first RNA region and said first DNA region are hybridized as a RNA/DNA heteroduplex. Said first strand further comprises a nucleic acid therapeutic oligonucleotide region that is capable of being cleaved from at least one nucleotide in said first RNA region. Methods for using the double-stranded nucleic acid agents include methods for delivering the therapeutic oligonucleotide as a single strand by cleaving it from at least a portion of the first RNA region. The methods further include delivering the double-stranded nucleic acid agent and thus the therapeutic oligonucleotide to a target site within the body of a treatment subject.

7 Claims, 25 Drawing Sheets

Specification includes a Sequence Listing.

(56) References Cited

OTHER PUBLICATIONS

Wahlestedt et al., Potent and nontoxic antisense oligonucleotides containing locked nucleic acids, PNAS, vol. 97, pp. 5633-5638. (Year: 2000).*
Bauman et al., Anti-tumor activity of splice-switching oligonucleotides, Nucleic Acids Research, vol. 38, pp. 8348-3856. (Year: 2010).*
Jearawiriyapaisarn et al., Sustained dystrophin expression induced by peptide-conjugated morpholino oligomers in the muscles of mdx mice, Molecular Therapy, vol. 16, pp. 1624-1629. (Year: 2008).*
International Search Report dated Aug. 26, 2014, in PCT/JP2014/002882.
Lima et al., "Single-Stranded siRNAs Activate RNAi in Animals," Cell, Aug. 31, 2012, 150:883-894.
Nishina et al. "Efficient In Vivo Delivery of siRNA to the Liver by Conjugation of α-Tocopherol," Molecular Therapy, Apr. 2008, 16(4):734-740.
Peer et al., "Systemic Leukocyte-Directed siRNA Delivery Revealing Cyclin D1 as an Anti-Inflammatory Target," Science, Feb. 1, 2008, 319:627-630.
Soutschek et al., "Therapeutic silencing of an endogenous gene by systemic administration of modified siRNAs," Nature, Nov. 11, 2004, 432:173-178.
Supplementary European Search Report dated Dec. 8, 2016, in EP 14804901.8.

* cited by examiner

[Fig. 1]
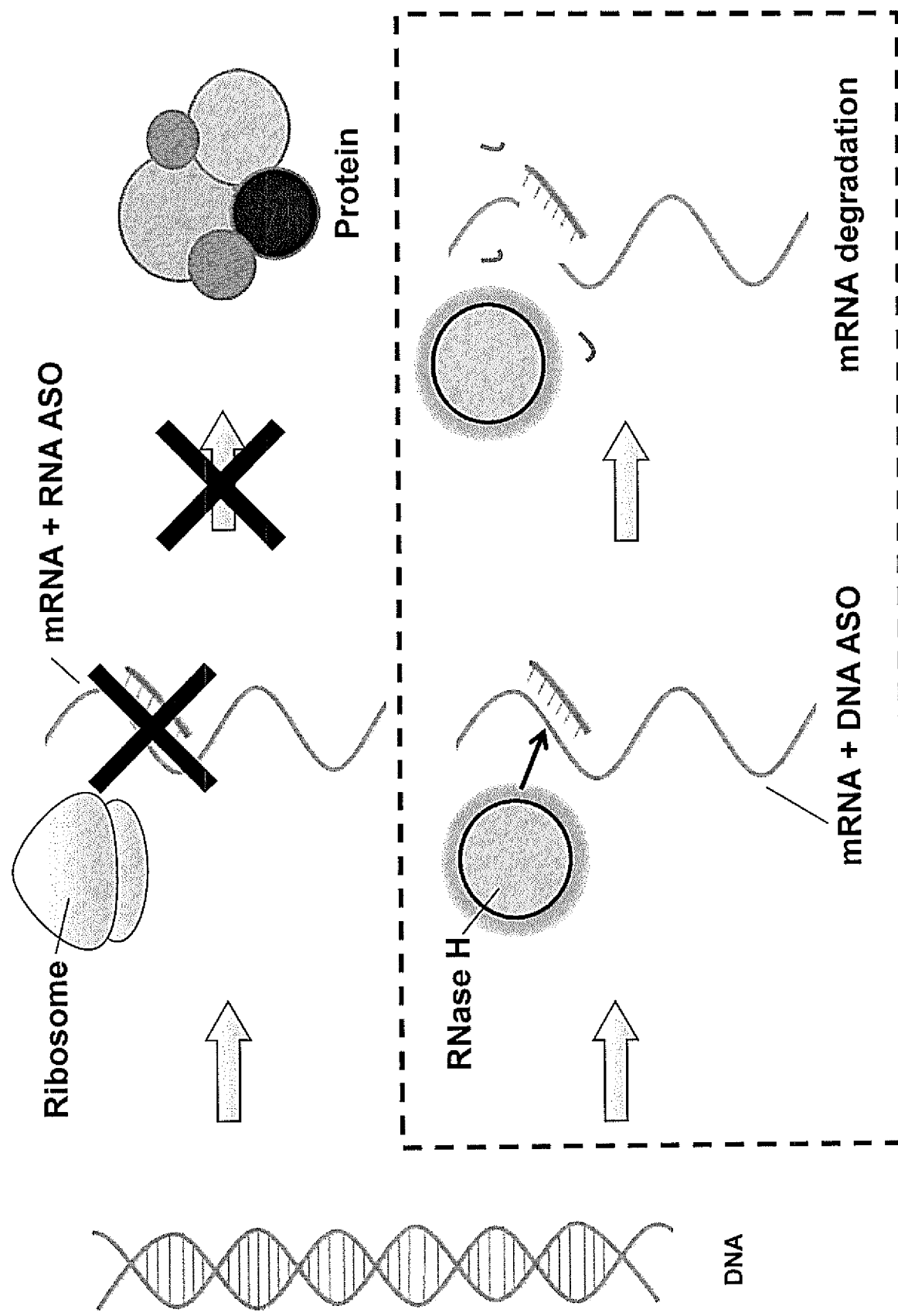

[Fig. 2]
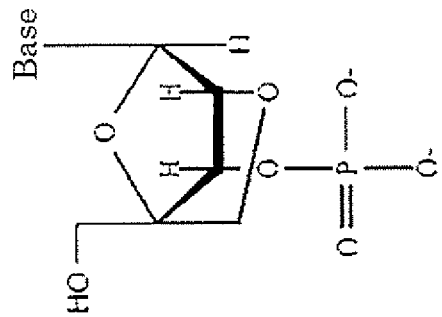
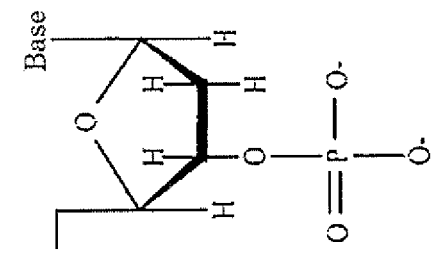
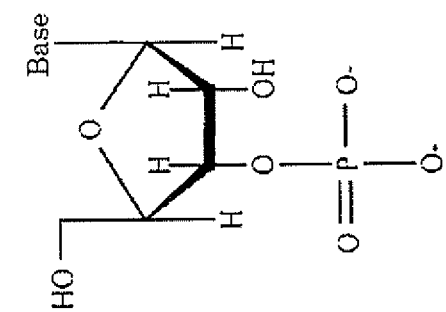
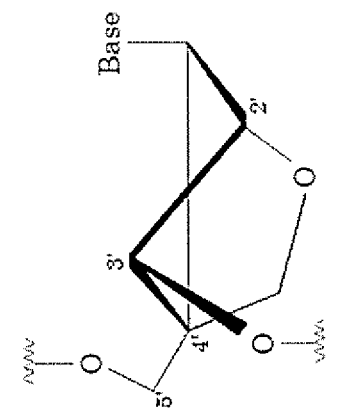
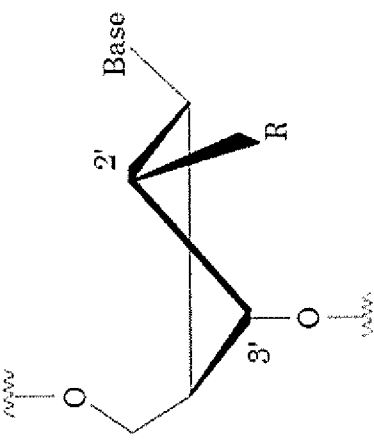
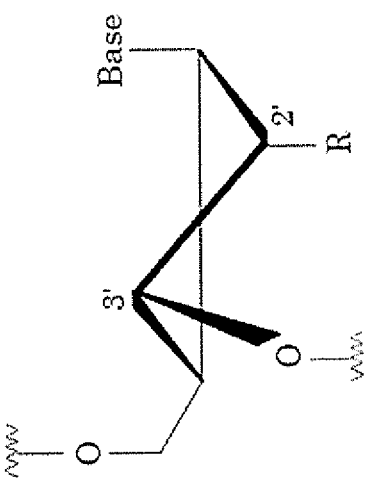

[Fig. 3]
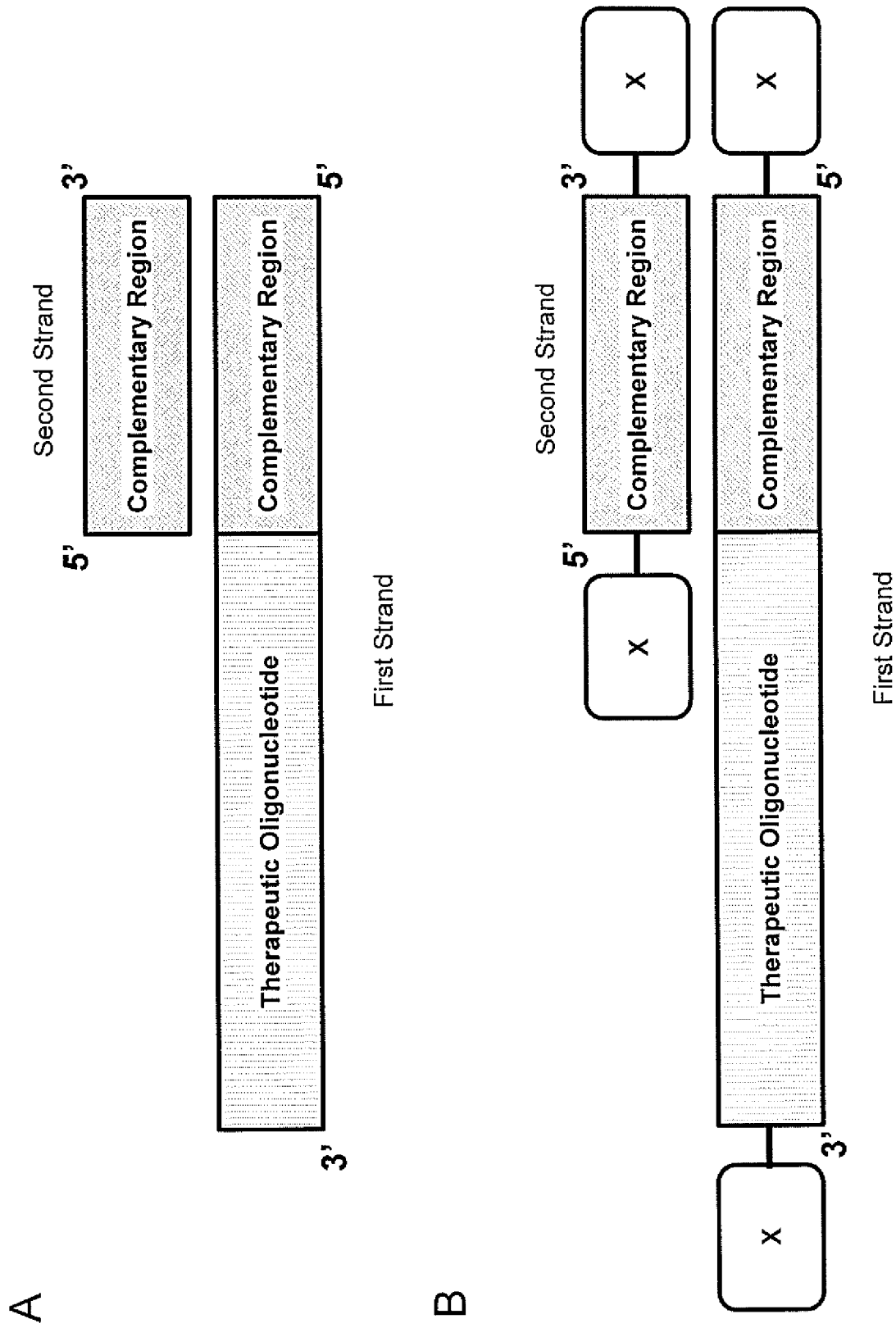

[Fig. 4]
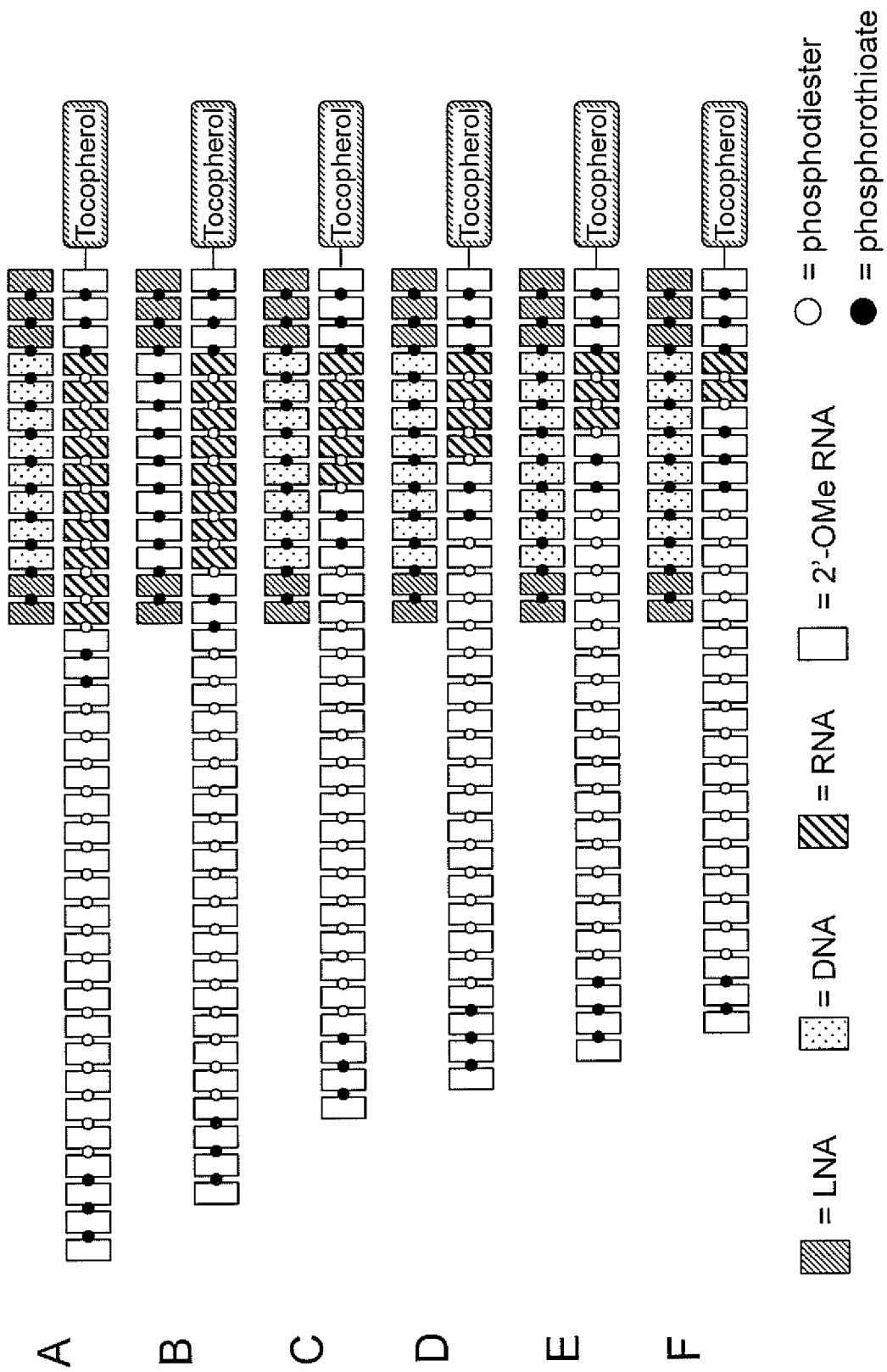

[Fig. 5]
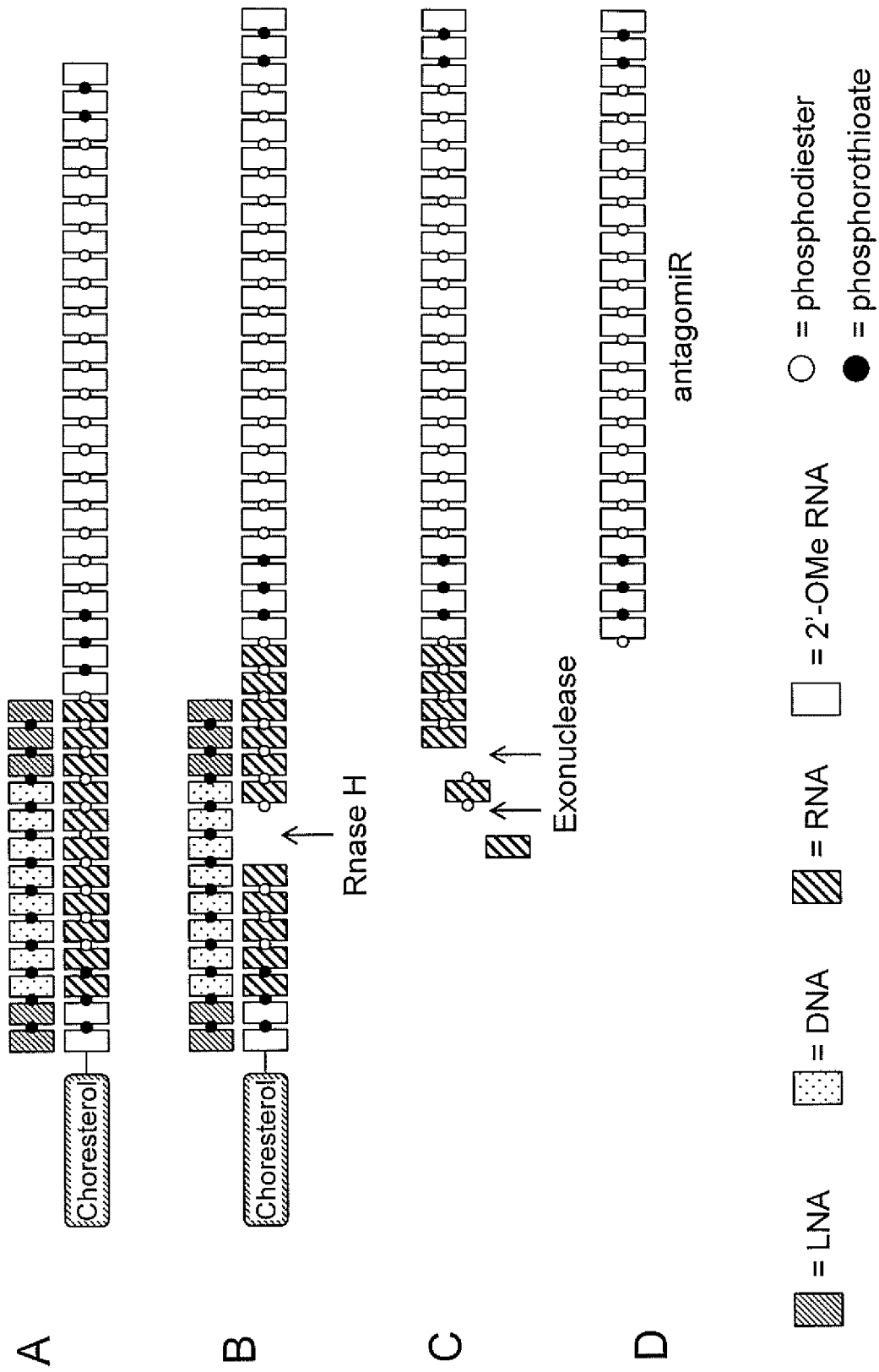

[Fig. 6]
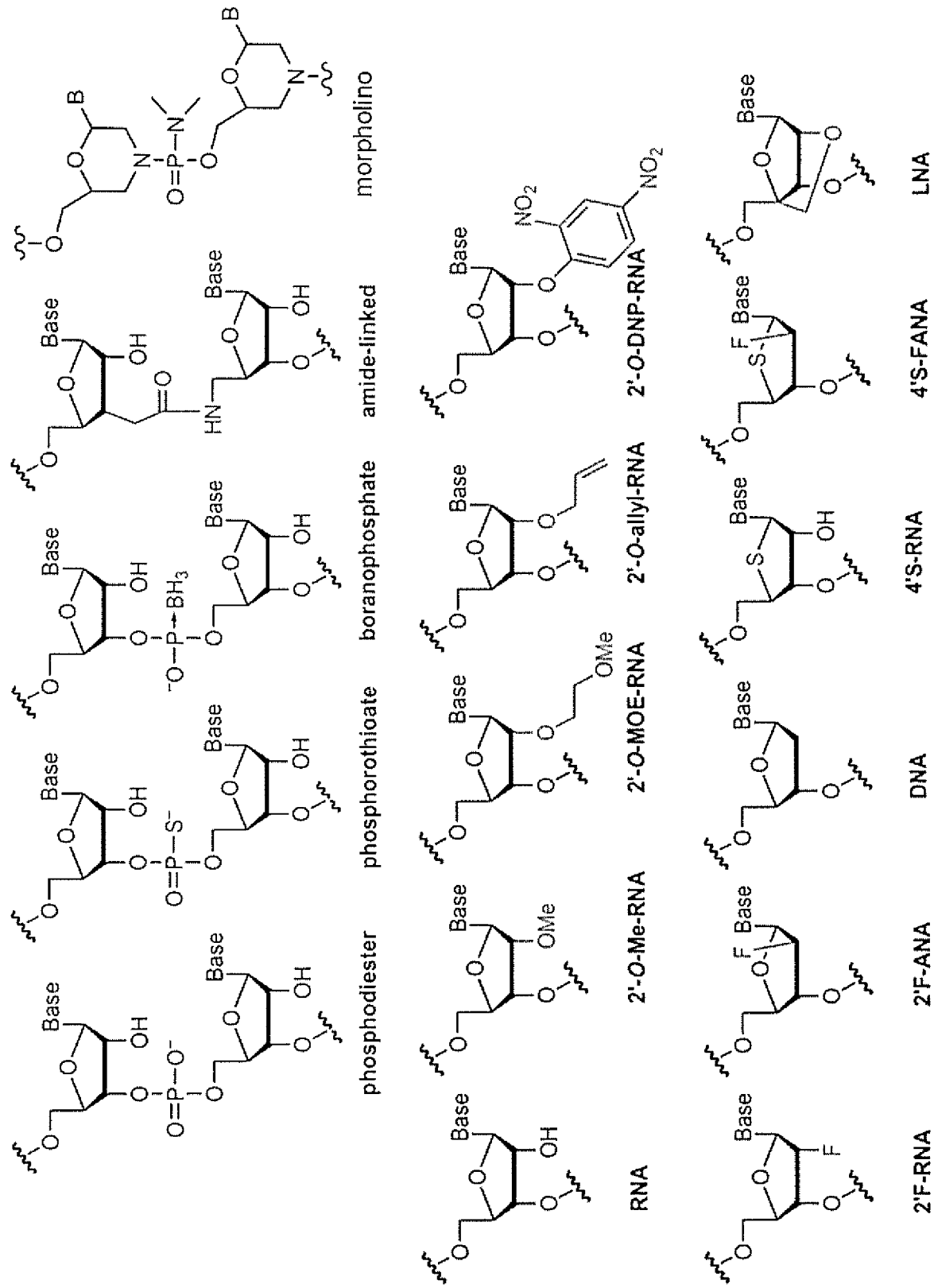

[Fig. 7-1]
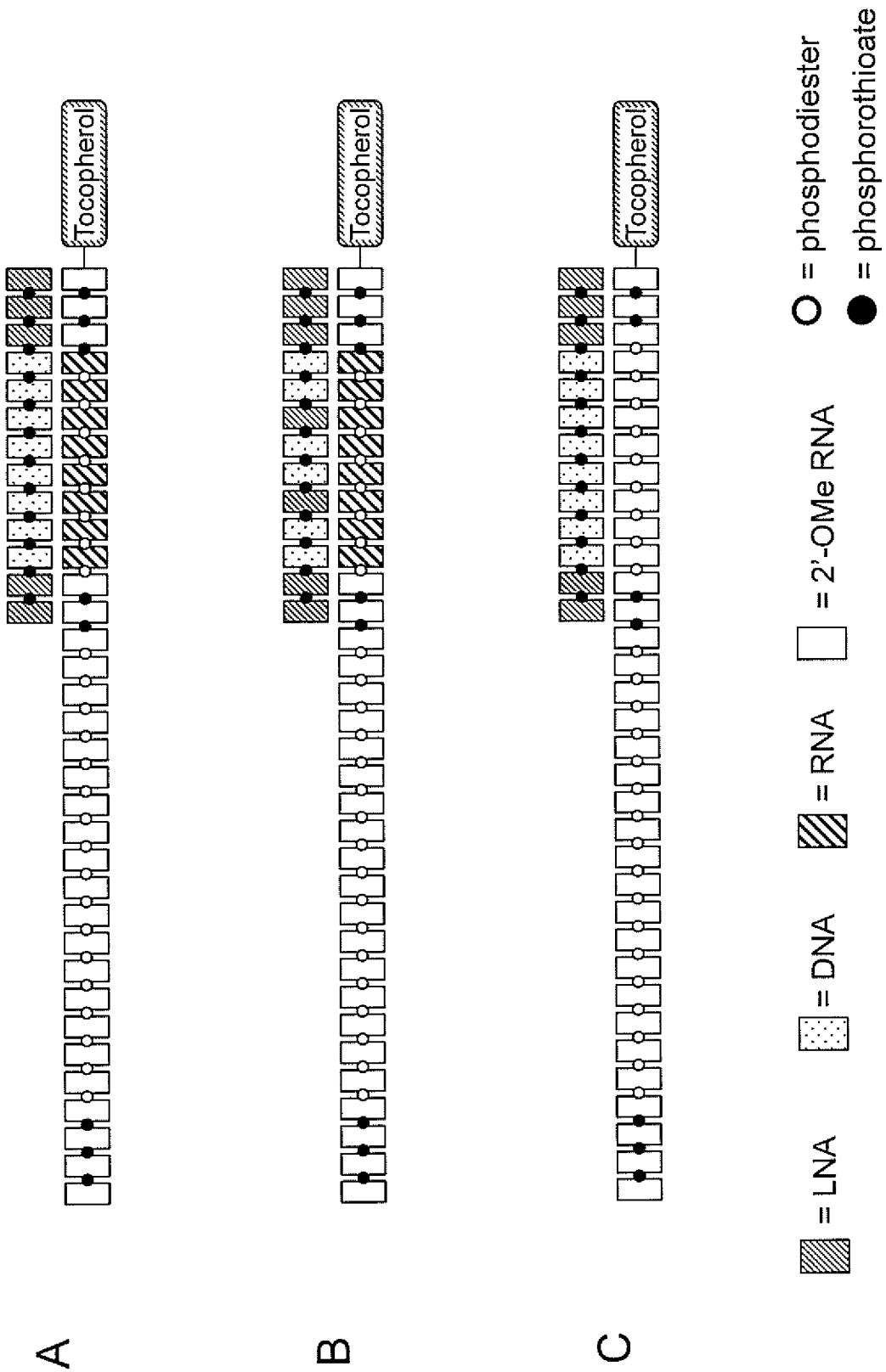

[Fig. 7-2]
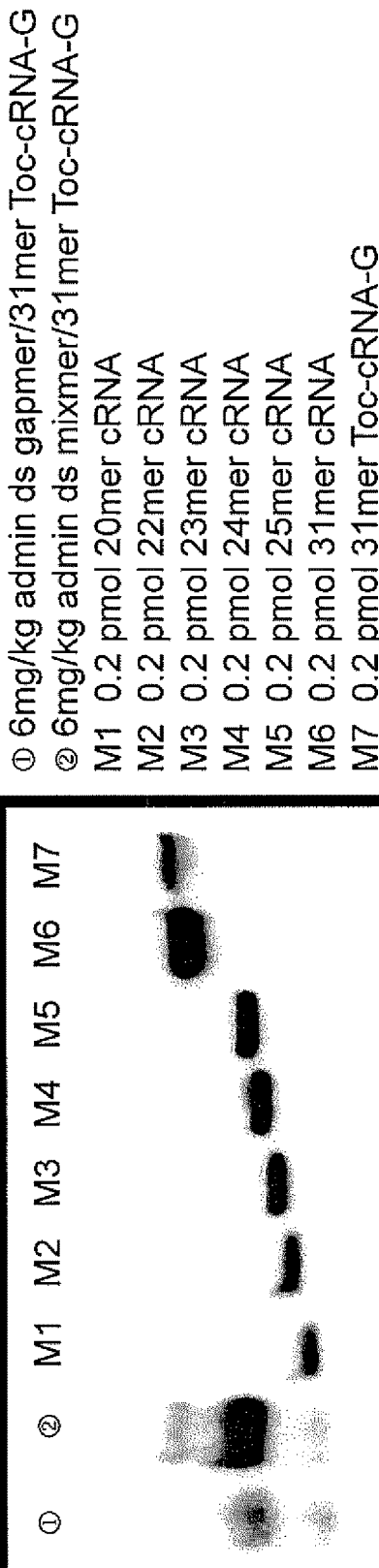
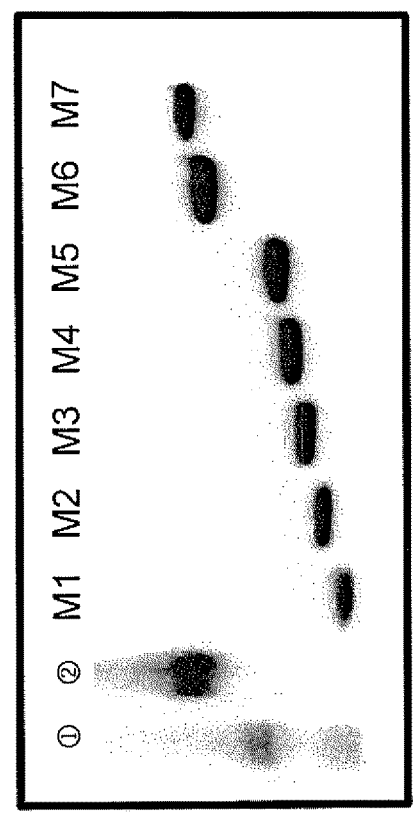

[Fig. 8]
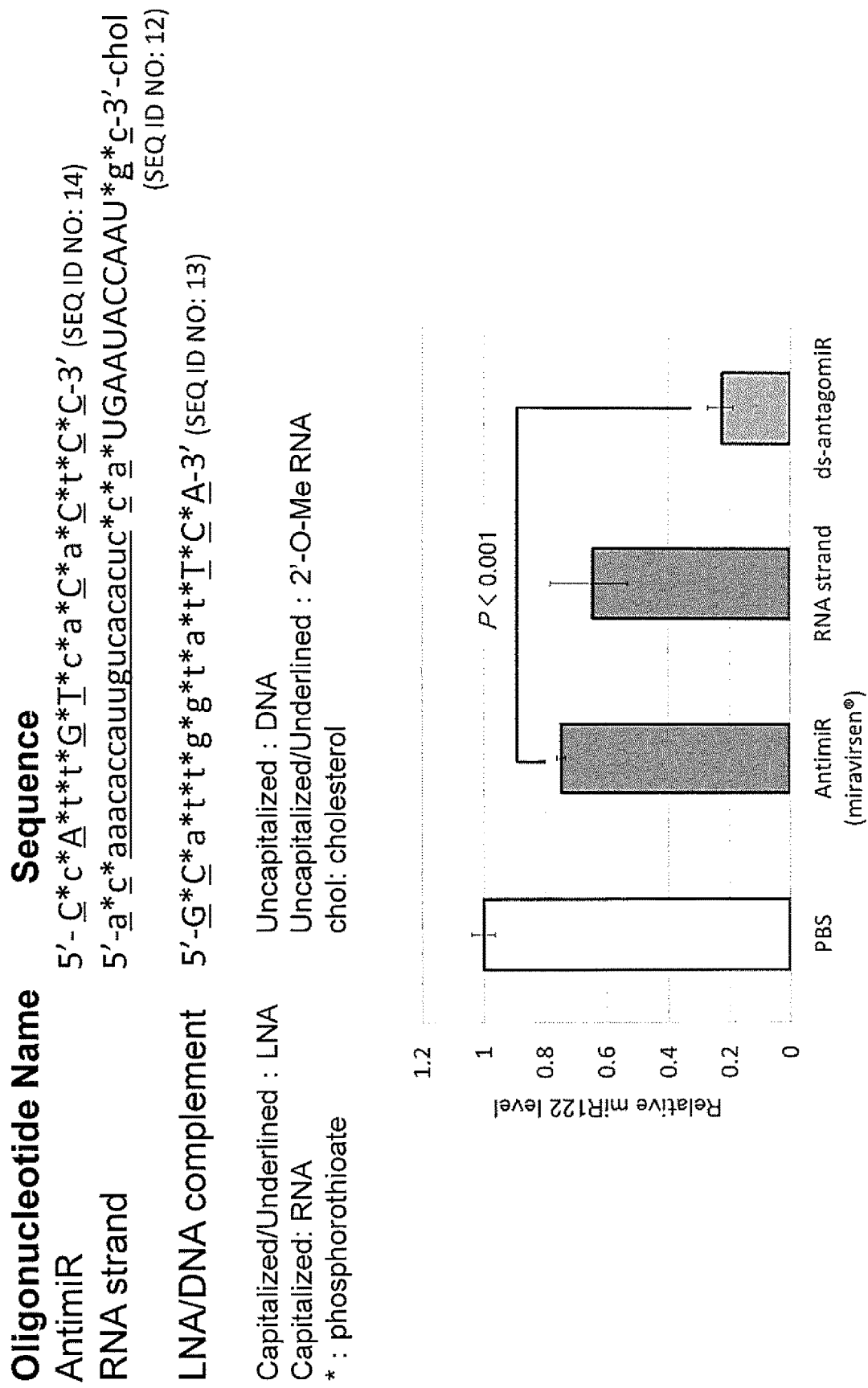

[Fig. 9]

| Oligonucleotide Name | Sequence |
|---|---|
| AntimiR | 5'- C*c*A*t*t*G*T*c*a*C*a*C*t*C*C-3' (SEQ ID NO: 14) |
| RNA strand | 5'-C*c*A*t*t*G*T*c*a*C*a*C*t*C*CGCGAUACCAAU*c*g-3' (SEQ ID NO: 15) |
| LNA/DNA complement | 5'-C*G*a*t*t*g*g*t*a*t*C*G*C-3' (SEQ ID NO: 16) |

Capitalized/Underlined : LNA    Uncapitalized : DNA
Capitalized: RNA    Uncapitalized/Underlined : 2'-O-Me RNA
* : phosphorothioate    chol: cholesterol

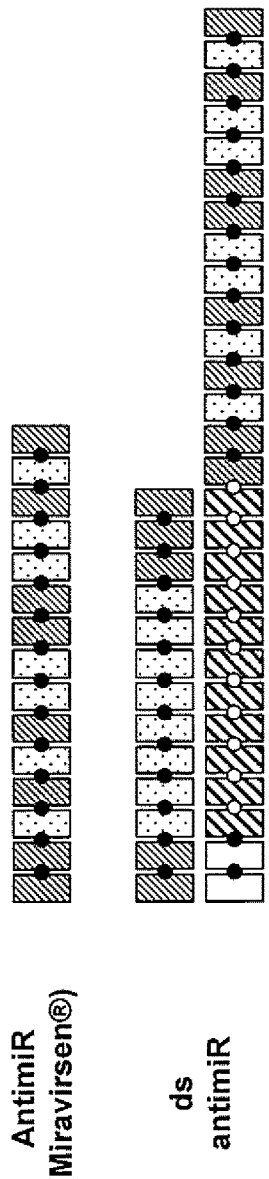

AntimiR (Miravirsen®)

ds antimiR

▨ = LNA   ⬚ = DNA   ▨ = RNA   ⬚ = 2'-OMe RNA

○ = phosphodiester
● = phosphorothioate

[Fig. 10a]
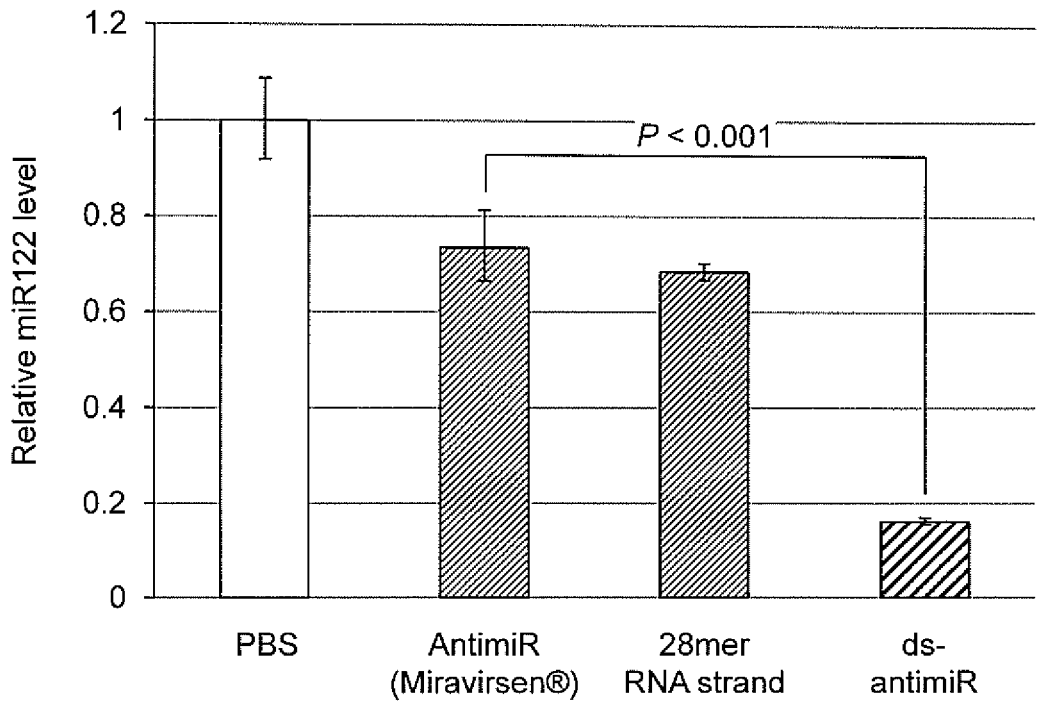
[Fig. 10b]
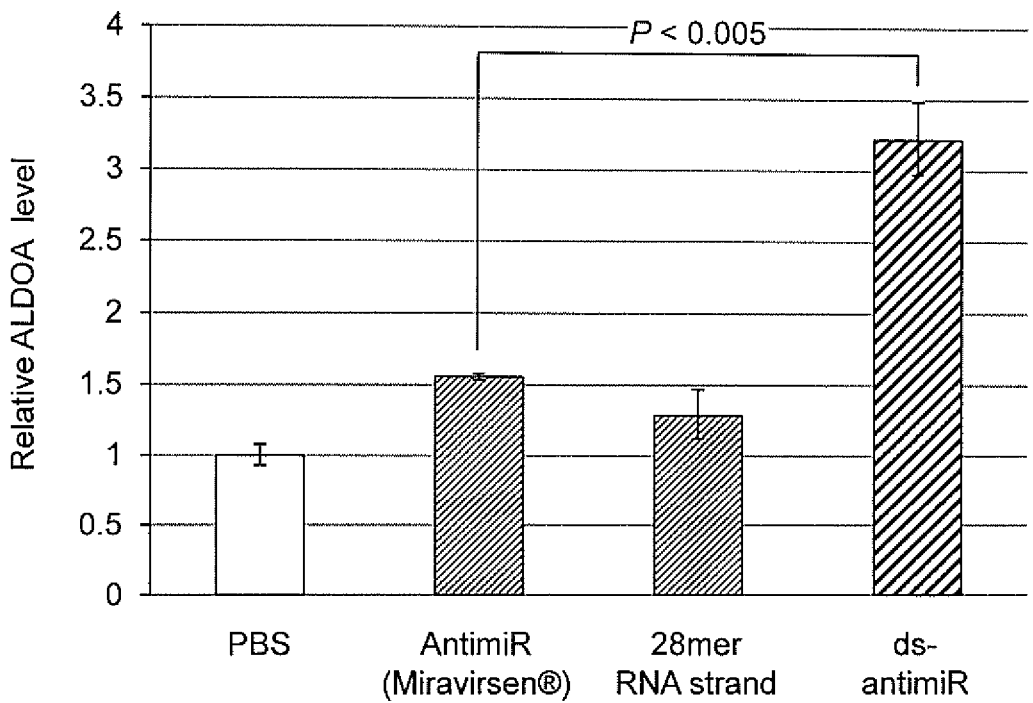

[Fig. 10c]
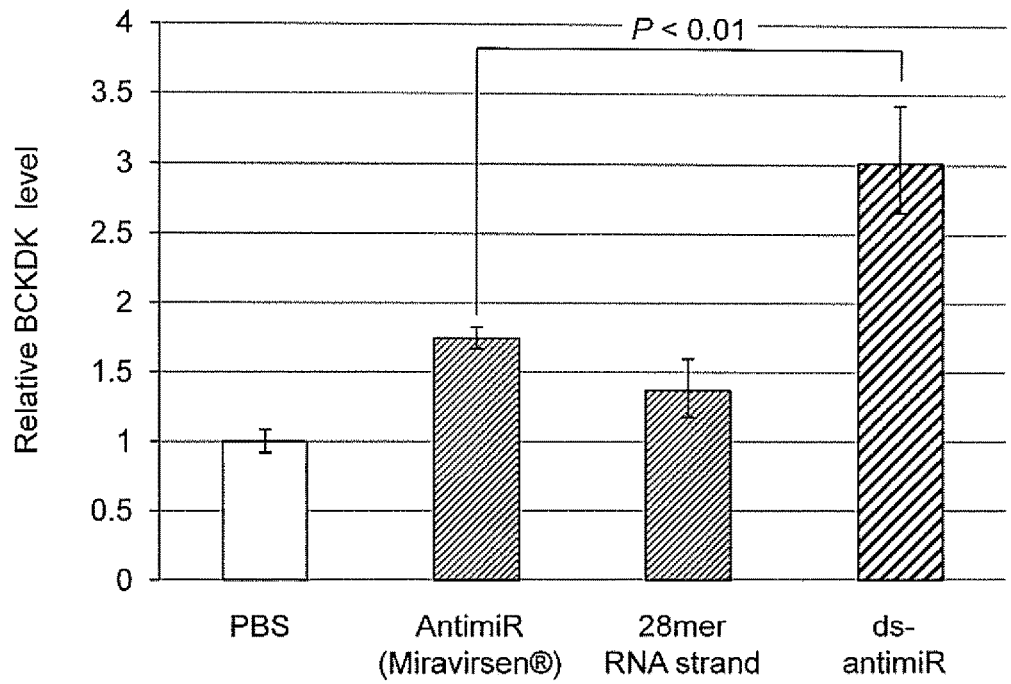
[Fig. 10d]
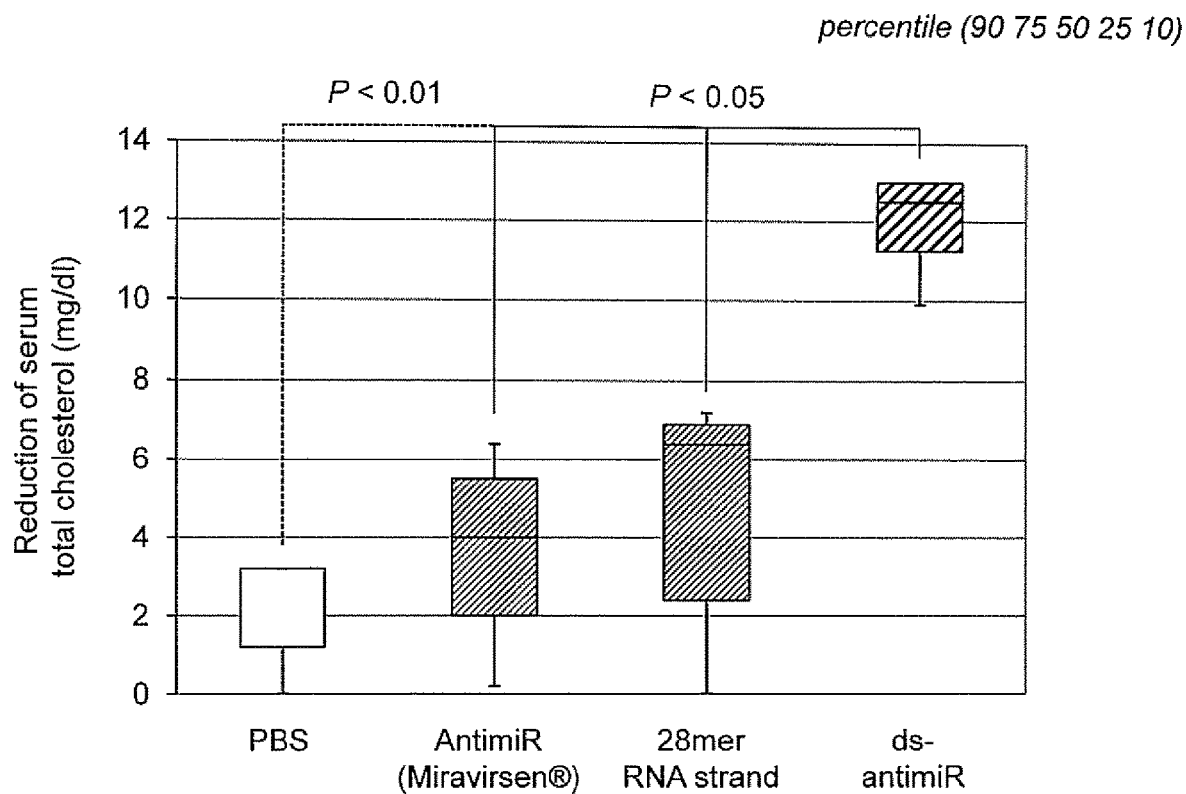

[Fig. 10e]
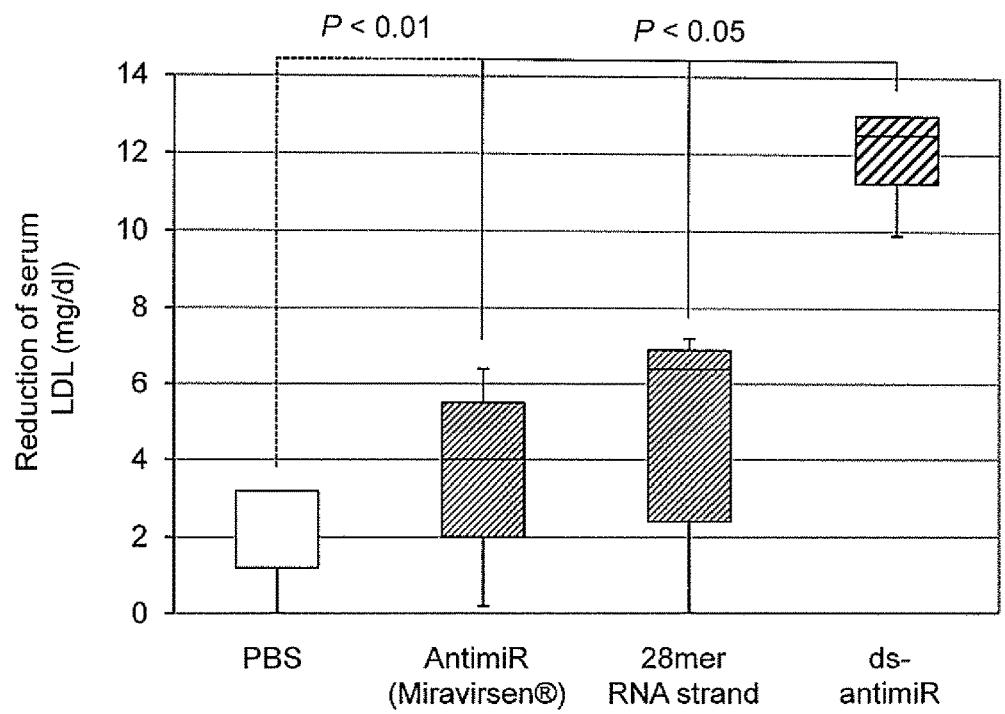
[Fig. 10f]
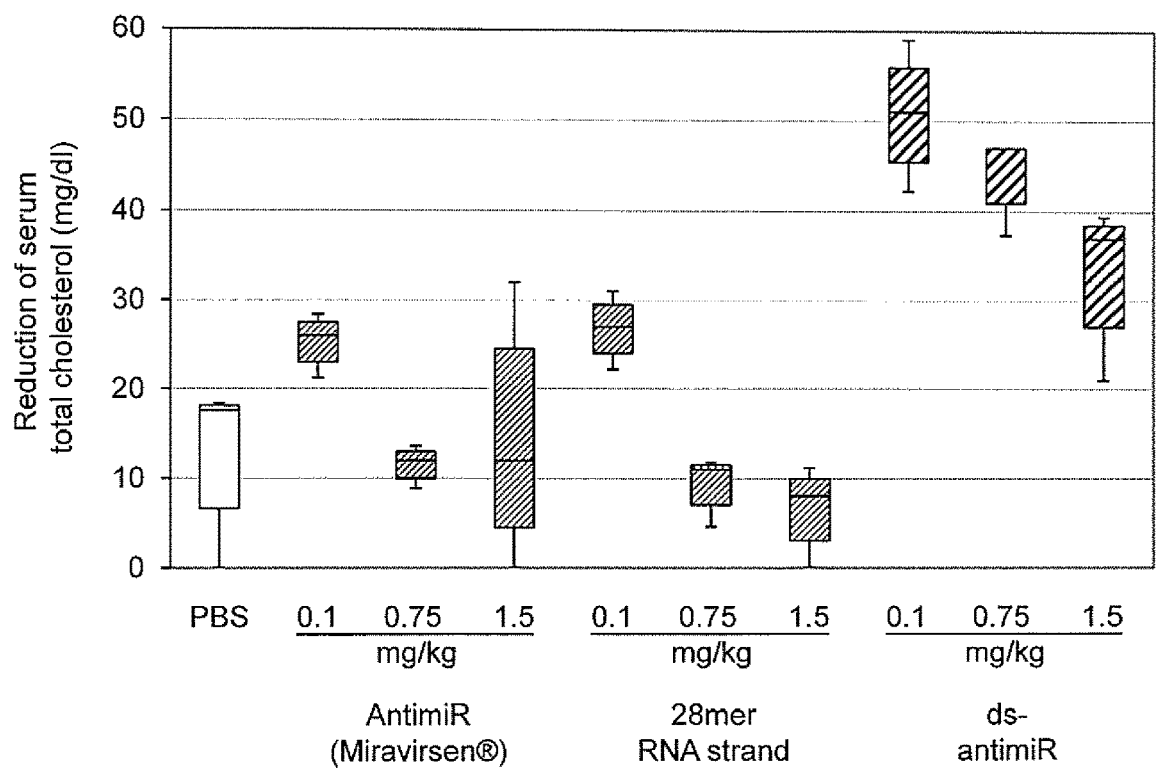

[Fig. 11]

| Oligonucleotide Name | Sequence |
|---|---|
| SSO | 5'- t*<u>C</u>*t*g*<u>G</u>*g*c*<u>T</u>*c*c*<u>T</u>*g*g*<u>T</u>*a-3' (SEQ ID NO: 18) |
| RNA strand | 5'-t*<u>C</u>*t*g*<u>G</u>*g*c*<u>T</u>*c*c*<u>T</u>*g*g*<u>T</u>*aGCGAUACCAAU*<u>c</u>*<u>c</u>*g-3' (SEQ ID NO: 17) |
| LNA/DNA complement | 5'-<u>C</u>*<u>G</u>*a*t*t*g*g*t*a*t*<u>C</u>*<u>G</u>*<u>C</u>-3' (SEQ ID NO: 16) |

Capitalized/Underlined : LNA  
Capitalized: RNA  
* : phosphorothioate

Uncapitalized : DNA  
Uncapitalized/Underlined : 2'-O-Me RNA  
chol: cholesterol

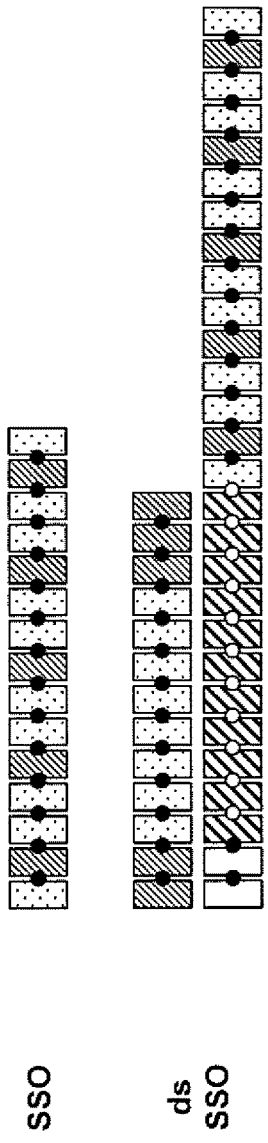

[Fig. 12]
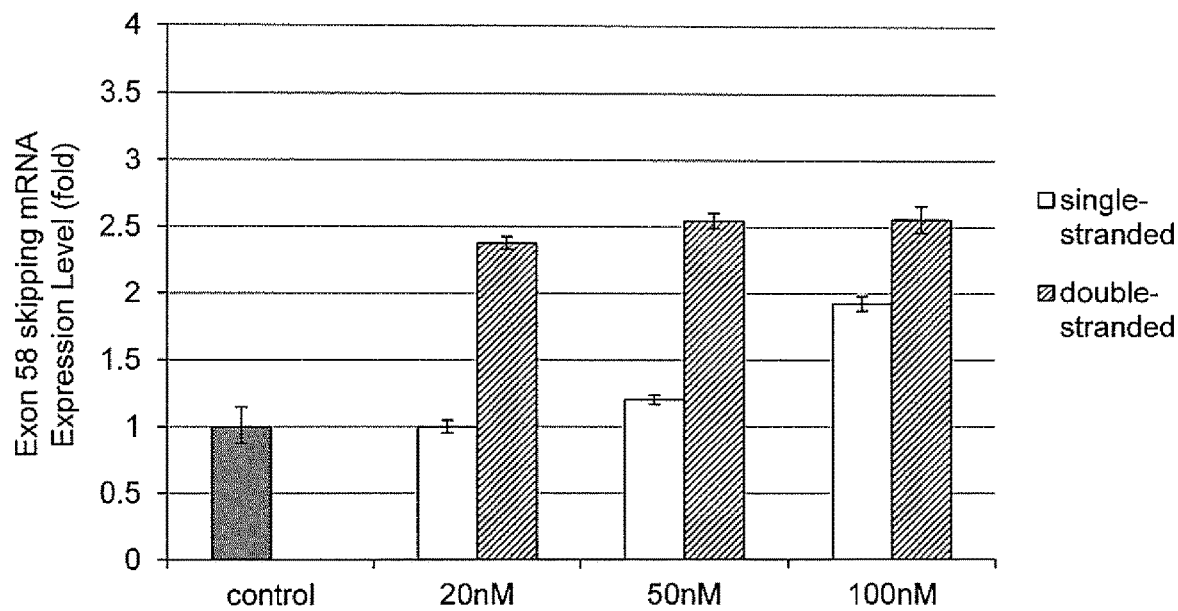

[Fig. 13]

| Oligonucleotide Name | Sequence |
|---|---|
| Intron gapmer | 5'-C*T*C*c*c*a*c*c*a*c*a*t*a*G*C*A-3' (SEQ ID NO: 36) |
| RNA strand | 5'-C*T*C*c*c*a*c*c*a*c*a*t*a*G*C*AGCGAUACCAAU*c*g-3' (SEQ ID NO: 35) |
| LNA/DNA complement | 5'-C*G*a*t*t*g*g*t*a*t*C*G*C-3' (SEQ ID NO: 16) |

Capitalized/Underlined : LNA  
Capitalized: RNA  
*: phosphorothioate

Uncapitalized : DNA  
Uncapitalized/Underlined : 2'-O-Me RNA  
chol: cholesterol Intron gapmer ds Intron gapmer ▨ = LNA    ▦ = DNA    ▨ = RNA    ☐ = 2'-OMe RNA ○ = phosphodiester  
● = phosphorothioate

[Fig. 14]
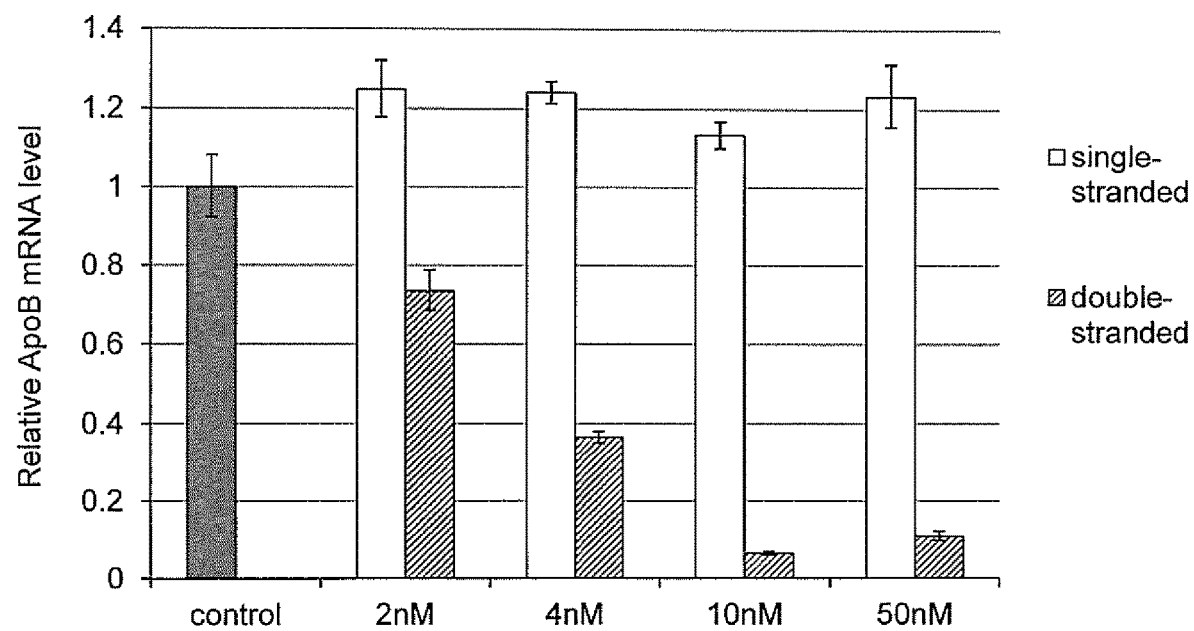

[Fig. 15]
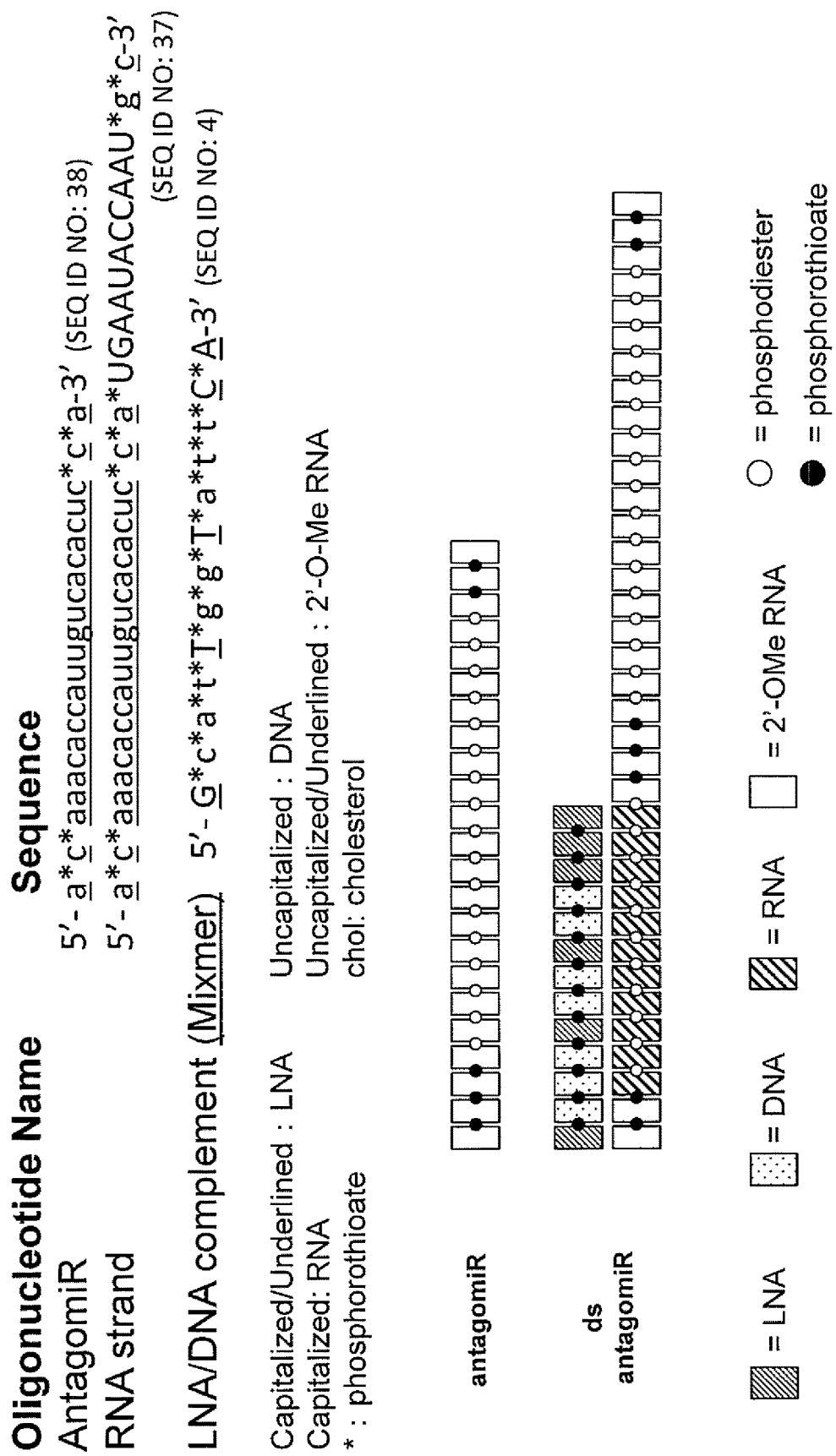

[Fig. 16]
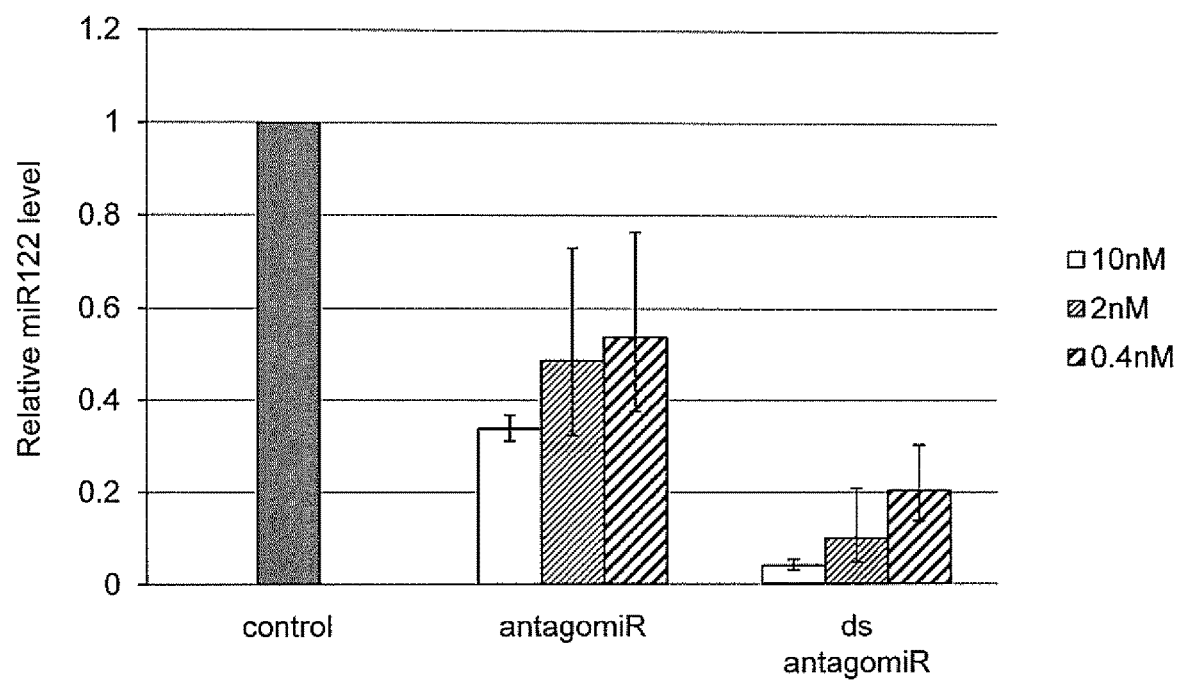

[Fig. 17]

| Oligonucleotide Name | Sequence |
|---|---|
| SSO | 5'- t*C*t*g*G*g*c*T*c*c*T*g*g*T*a-3' (SEQ ID NO: 18) |
| RNA strand | 5'- t*C*t*g*G*g*c*T*c*c*T*g*g*T*aGCGAUACCAAU*c*g-3' (SEQ ID NO: 17) |
| LNA/DNA complement (Mixmer) | 5'- G*c*a*t*T*g*g*T*a*t*t*C*A-3' (SEQ ID NO: 4) |

Capitalized/Underlined : LNA    Uncapitalized : DNA
Capitalized: RNA    Uncapitalized/Underlined : 2'-O-Me RNA
* : phosphorothioate    chol: cholesterol

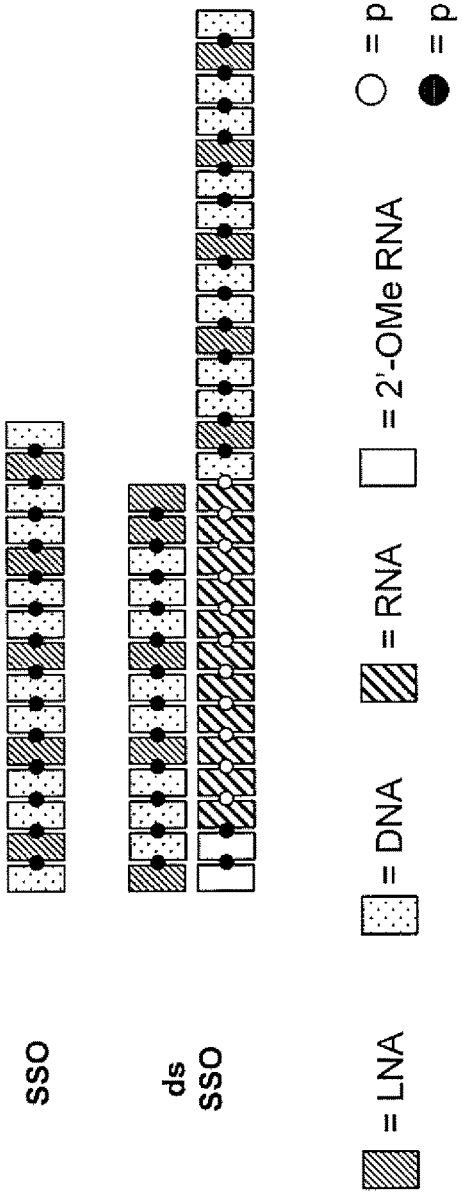

○ = phosphodiester
● = phosphorothioate

▨ = LNA    ▦ = DNA    ▧ = RNA    ▢ = 2'-OMe RNA

[Fig. 18]
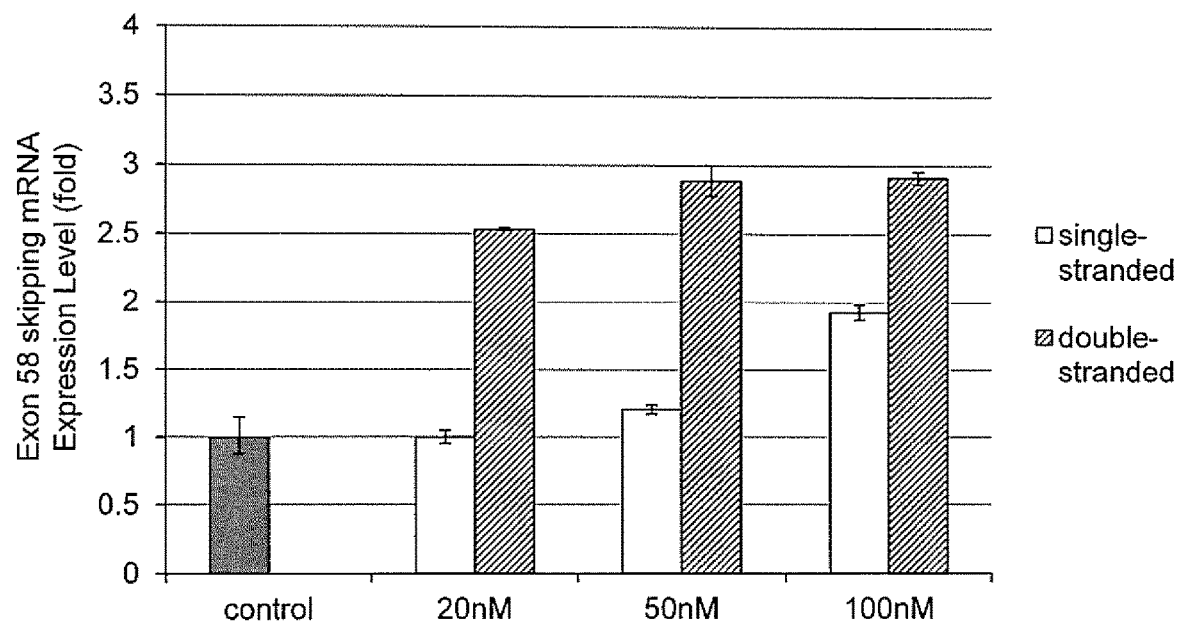

[Fig. 19]

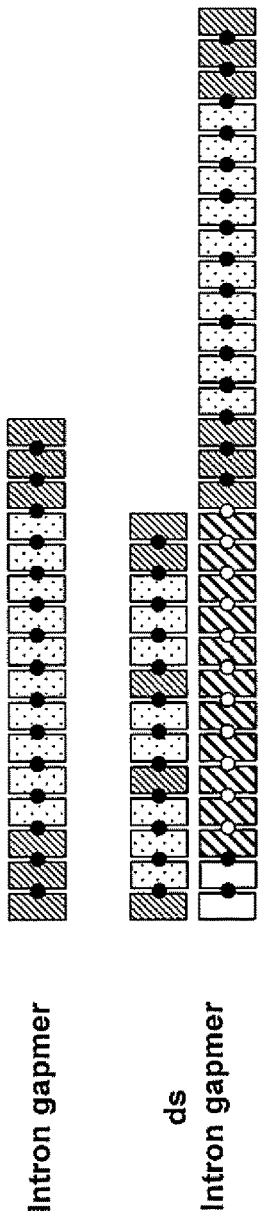

| Oligonucleotide Name | Sequence |
|---|---|
| Intron gapmer | 5'-C*T*C*c*c*a*c*c*a*c*a*t*a*G*C*A-3' (SEQ ID NO: 36) |
| RNA strand | 5'-C*T*C*c*c*a*c*c*a*c*a*t*a*G*C* AGCGAUACCAAU*c*g-3' (SEQ ID NO: 35) |
| LNA/DNA complement (Mixmer) | 5'-G*c*a*t*T*g*g*T*a*t*t*C*A-3' (SEQ ID NO: 4) |

Capitalized/Underlined : LNA     Uncapitalized : DNA
Capitalized: RNA     Uncapitalized/Underlined : 2'-O-Me RNA
*: phosphorothioate     chol: cholesterol Intron gapmer ds Intron gapmer ▨ = LNA    ▧ = DNA    ▨ = RNA    □ = 2'-OMe RNA    ○ = phosphodiester    ● = phosphorothioate

[Fig. 20]
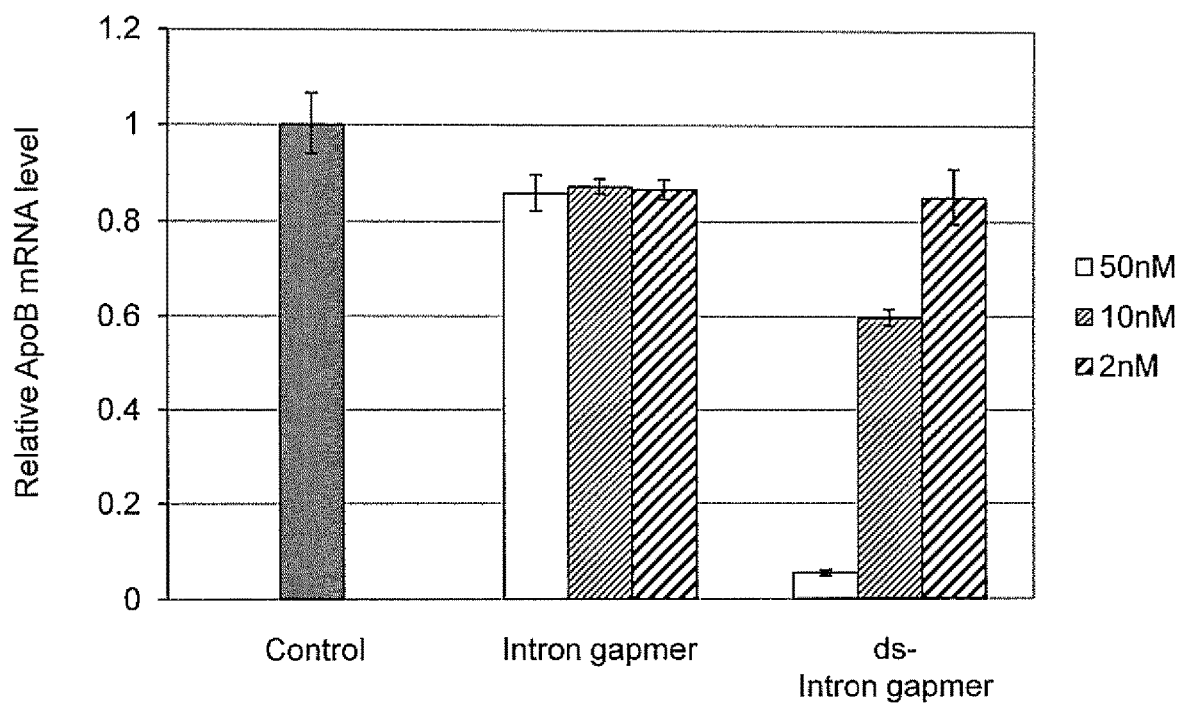

[Fig. 21]

| Oligonucleotide Name | Sequence |
|---|---|
| AntimiR | 5'- C*c*A*t*t*G*T*c*a*C*a*C*t*C*C-3' (SEQ ID NO: 14) |
| RNA strand-5' | 5'-C*c*A*t*t*G*T*c*a*C*a*C*t*C*CGGAUACCAAU*c*g-3' (SEQ ID NO: 15) |
| RNA strand-3' | 5'-g*c*g*AUACCAAUCGC*c*A*t*t*G*T*c*a*C*a*C*t*C*C-3' (SEQ ID NO: 39) |
| LNA/DNA complement | 5'-C*G*a*t*t*g*g*t*a*t*C*G*C-3' (SEQ ID NO: 16) |

Capitalized/Underlined : LNA
Capitalized: RNA
*: phosphorothioate

Uncapitalized : DNA
Uncapitalized/Underlined : 2'-O-Me RNA
chol: cholesterol

AntimiR (Miravirsen®)

ds antimiR-5' ds antimiR-3'

▨ = LNA   ▦ = DNA   ▧ = RNA   ☐ = 2'-OMe RNA   ○ = phosphodiester   ● = phosphorothioate

[Fig. 22]
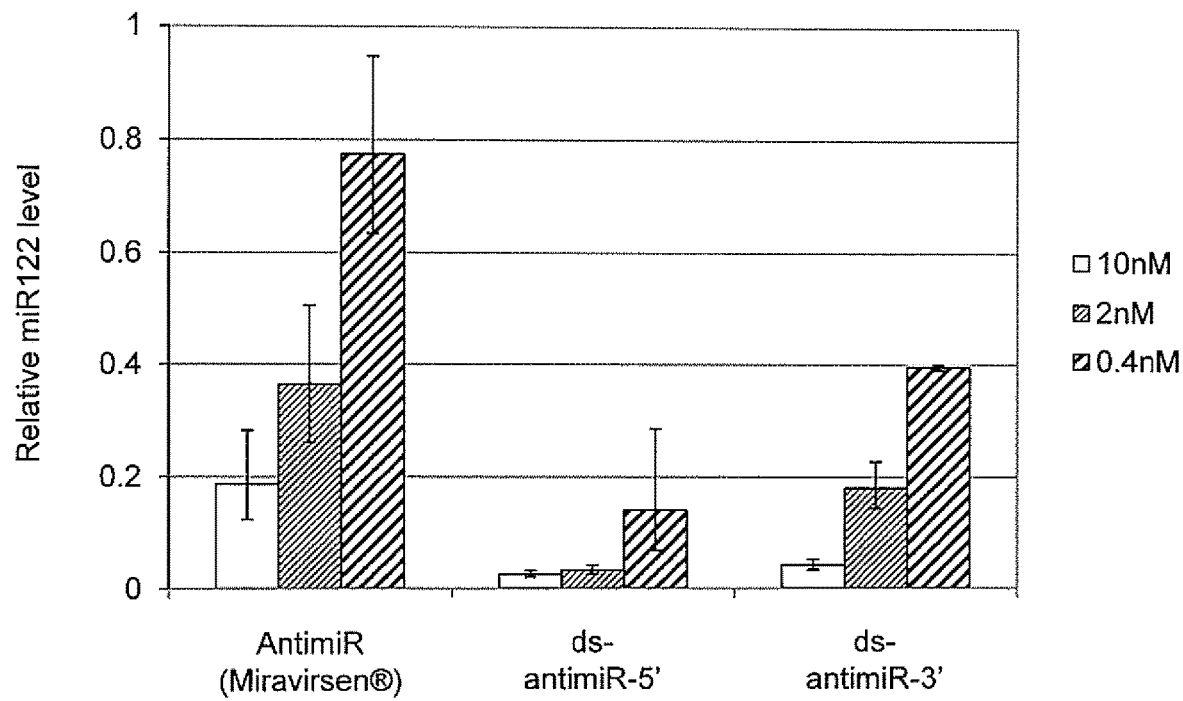

DOUBLE-STRANDED AGENTS FOR DELIVERING THERAPEUTIC OLIGONUCLEOTIDES

CROSS-REFERENCE TO RELATED APPLICATIONS

This application is a National Stage application of PCT/JP2014/002882, filed May 30, 2014, which claims priority from U.S. Provisional Application 61/829,239, filed May 30, 2013.

TECHNICAL FIELD

The present application relates to a double-stranded nucleic acid agent useful for delivering therapeutic oligonucleotides to a cell, such as in a biological sample or a patient. Therapeutic oligonucleotides may include antisense oligonucleotides, antagomirs, splice switching oligonucleotides, single-stranded siRNAs, microRNAs, pre-microRNAs, and the like. The therapeutic oligonucleotide is a constituent part of one of the strands of the double-stranded agent, and is released, at least in part by the action of enzymes or by the unwinding of the double-stranded structure. The therapeutic oligonucleotides can be used for any of the purposes known for such oligonucleotides, which include, for example, modifying RNA transcription levels or protein levels in cells.

BACKGROUND ART

In recent years, oligonucleotides have been a subject of interest in the on-going development of pharmaceutical products called nucleic acid drugs, and particularly, from the viewpoints of high selectivity of target gene and low toxicity, the development of nucleic acid drugs utilizing an antisense method is actively underway. The antisense method includes methods of selectively modifying or inhibiting the expression of a protein that is encoded by a target gene, by introducing into a cell an oligonucleotide (e.g., an antisense oligonucleotide, or ASO) that is complementary to a partial sequence of the mRNA (sense strand) of a target gene. Similarly, antisense methods also target miRNA and operate to modify the activity of such miRNA.

As illustrated in FIG. 1 (upper portion), when an oligonucleotide comprising RNA is introduced into a cell as an ASO, the ASO binds to a transcription product (mRNA) of the target gene, and a partial double strand is formed. It is known that this double strand plays a role as a cover to prevent translation by a ribosome, and thus the expression of the protein encoded by the target gene is inhibited.

On the other hand, when an oligonucleotide comprising a DNA is introduced into a cell as an ASO, a partial DNA-RNA hetero-duplex is formed. Because this structure is recognized by RNase H, and the mRNA of the target gene is thereby decomposed, the expression of the protein encoded by the target gene is inhibited. (FIG. 1, lower portion). In many cases, the gene expression suppressing effect is higher when DNA is used as an ASO (RNase H-dependent route), as compared with the case of using an RNA ASO.

When utilizing an oligonucleotide as a nucleic acid drug, various nucleic acid analogs such as Locked Nucleic Acid (LNA) (registered trademark), other bridged nucleic acids (BNA), and the like have been developed to enhance binding affinity to target RNA and stability in vivo.

As illustrated in FIG. 2, since the sugar moiety of a natural nucleic acid (RNA or DNA) has a five-membered ring with four carbon atoms and one oxygen atom, the sugar moiety has two kinds of conformations, an N-form and an S-form. It is known that these conformations swing from one to the other, and thereby, the helical structure of the nucleic acid also adopts different forms, an A-form and a B-form. Since the mRNA that serves as the target of the aforementioned ASO adopts a helical structure in the A-form, with the sugar moiety being mainly in the N-form, it is important for the sugar moiety of the ASO to adopt the N-form from the viewpoint of increasing the affinity to RNA. A product that has been developed under this concept is a modified nucleic acid such as a LNA (2'-O, 4'-C-methylene-bridged nucleic acid (2',4'-BNA)). For example, in the LNA, as the oxygen at the 2'-position and the carbon at the 4'-position are bridged by a methylene group, the conformation is fixed to the N-form, and there is no more fluctuation between the conformations. Therefore, an oligonucleotide synthesized by incorporating several units of LNA has very high affinity to RNA and very high sequence specificity, and also exhibits excellent heat resistance and nuclease resistance, as compared with oligonucleotides synthesized with conventional natural nucleic acids (see Patent Document 1). Since other artificial nucleic acids also have such characteristics, much attention has been paid to artificial nucleic acids in connection with the utilization of an antisense method and the like (see Patent Documents 1 to 9).

Nonetheless, the designs of antisense oligonucleotides using even these high-performance modified nucleic acids still lack suitable efficiency, potency, and/or safety for use as therapeutic agents.

One technical issue limiting the use of therapeutic oligonucleotides is the inability to efficiently deliver the agent to a site where it can elicit an effect. For some types of therapeutic oligonucleotides, direct delivery of the agent itself can reach the site of activity, but large doses are generally required and that compromises the safety. The reasons for inefficient deliver may include metabolic instability, inefficient transport, and non-specific trapping or binding interactions that sequester the agents. Other types, such as short interfering RNA duplexes (siRNA), require complex lipid formulations for delivery but these are reported to be expensive, difficult to prepare, and to have some toxic side-effects (Non-Patent Document 1). Thus there is a recognized need for more efficient methods to deliver oligonucleotide therapeutics to cells and tissues in a biological sample or in a patient.

Furthermore, when an antisense oligonucleotide is used as a drug, for some applications it is also important that the relevant oligonucleotide can be delivered to a target site with high specificity and high efficiency. Methods for delivering an oligonucleotide include using lipids such as cholesterol and vitamin E (Non-Patent Documents 2 and 3), using a receptor-specific peptide such as RVG-9R (Non-Patent Document 4), or using an antibody specific to the target site (Non-Patent Document 5).

CITATION LIST

Patent Literature

PTL 1: JP 10-304889 A
PTL 2: WO 2005/021570
PTL 3: JP 10-195098 A
PTL 4: JP 2002-521310 W

PTL 5: WO 2007/143315
PTL 6: WO 2008/043753
PTL 7: Patent Document 7: WO 2008/029619
PTL 8: WO 2003/011887
PTL 9: WO 2007/131238

Non Patent Literature

NPL 1: Walt F. Lima et al., Cell, Vol. 150, 883-894 (2012)
NPL 2: Kazutaka Nishina et al., Molecular Therapy, Vol. 16, 734-740 (2008)
NPL 3: Jurgen Soutscheck et al., Nature, Vol. 432, 173-178 (2004)
NPL 4: Kazutaka Nishina et al., Molecular Therapy, Vol. 16, 734-740 (2008)
NPL 5: Dan Peer et al., Science, Vol. 319, 627-630 (2008)

SUMMARY OF INVENTION

Technical Problem

An object of the present invention is to provide a double-stranded nucleic acid agent that can deliver a therapeutic oligonucleotide.

Solution to Problem

A double-stranded nucleic acid agent that can deliver a therapeutic oligonucleotide is provided which comprises a first and a second strand, wherein the therapeutic oligonucleotide is a portion of the first strand. The therapeutic oligonucleotide is generally a single-stranded agent, but can itself be a double-stranded or a hairpin construct. The therapeutic oligonucleotide is in some embodiments designed to elicit an antisense effect. For example, the antisense effect may be directed against a protein-encoding or non-protein encoding transcription product. The double-stranded nucleic acid agent may thus be applied to change the concentration or level of activity of the targeted transcription product. In some embodiments, the agent can be used to treat, prevent, or ameliorate a disease or condition in a patient that is characterized by having an abnormal level of a transcription product.

As shown in FIGS. 3A and 3B, the first strand comprises the therapeutic oligonucleotide region and a first complementary region. The first complementary region is complementary to a portion or the whole of the second strand. The second strand comprises a second complementary region. The second complementary region is complementary to a portion or the whole of the first complementary region, and optionally may be complementary to a portion of the therapeutic region. It is not required, however, that the first complementary region be full complementary to, or have the same number of bases as the second complementary region.

The therapeutic oligonucleotide region may be linked to 3' end of the complementary region of the first strand as shown in FIGS. 3A and 3B, or 5' end of the complementary region of the first strand as shown in FIG. 5. Preferably, the therapeutic oligonucleotide region may be linked to 5' end of the complementary region of the first strand.

The double-stranded nucleic acid agent in some embodiments further comprises a functional moiety, as shown in FIG. 3B. The functional moiety (x) may be a detection label, a delivery or targeting molecule, or a purification tag. One or more such moieties, from one or more of such categories can be joined to the double-stranded nucleic acid agent. In some embodiments, such moieties are joined at the terminal position, at the 3' or the 5' end of a nucleic acid strand. In other embodiments, a moiety may be joined at an internal position. A moiety may also be joined to a strand via a cleavable linker. In some embodiments one or more functional moieties enhance the delivery of the double-stranded nucleic acid agent to a target site with high specificity and high efficiency.

The second strand may be composed of one type of nucleotide or nucleotide analog (collectively, "base"), or it may be composed of two or more types of bases. When composed of two or more types, the bases can be arranged in a gapmer or a mixmer structure. For example, as a gapmer, the second strand may be arranged to have a center region consisting of at least 4 consecutive DNA nucleotides, a first 5'-wing region comprising at least two nucleotide analogs located on 5' terminal side of the central region, and a first 3'-wing region at least two nucleotide analogs located on 3' terminal side of the region as described with respect to the antisense strand in PCT/JP2012/083180, entitled "Chimeric Double-Stranded Nucleic Acid," which is incorporated herein by reference in its entirety. For example, as a mixmer, the second strand may be arranged to have no region consisting of 4 or more consecutive DNA nucleotides. The strand may also be composed of nucleotides or nucleotide analogs that are arranged in a double wing structure, such as is disclosed in co-pending and commonly owned U.S. Provisional Appl. No. 61/771,115, entitled "Chimeric Single-Stranded Antisense Polynucleotides," and U.S. Provisional Appl. No. 61/806,887, entitled "Double-Stranded Antisense Agents," which are incorporated herein by reference in their entirety. For example, as a double wing structure, the second strand may be arranged to comprising:
a center nucleotide region comprising at least 4 DNA nucleotides;
a first 5'-wing region joined to the 5' end of the center nucleotide region comprising 1-10 nucleotides wherein at least 1 is a nucleotide analog;
a first 3'-wing region joined to the 3' end of the center nucleotide region comprising 1-10 nucleotides wherein at least 1 is a nucleotide analog; and
a second 5'-wing region and/or a second 3'-wing region, wherein:
the second 5'-wing region is joined to the 5' end of the first 5'-wing region, has higher resistance to DNase or RNase than a natural DNA or RNA and is missing in a cell when the chimeric polynucleotide delivered; and
the second 3'-wing region is joined to the 3' end of the first 3'-wing region, has higher resistance to DNase or RNase than a natural DNA or RNA. The second strand may also comprise peptide nucleic acid (PNA) units in whole or in part. The second strand may itself be an antisense oligonucleotide.

Generally, the second strand is designed to be resistant to nuclease degradation, or more generally, metabolic degradation, when put into a biological sample (cell, tissue, animal, human, etc.)

The first strand may be composed of one type of nucleotide or nucleotide analog (collectively, "base"), or it may be composed of two or more types of bases. As noted, the first strand comprises a first complementary region and a therapeutic oligonucleotide region. These regions are named simply for a convenient way to reference each portion of the strand. Some individual nucleotides and/or nucleotide analogues may be part of both regions. Thus the regions may "overlap" wherein a particular base both is complementary to a base in the second strand but also is part of the therapeutic oligonucleotide. For example, as illustrated in FIGS. 4A-4F, the therapeutic oligonucleotide may have no overlap with the second strand (FIG. 4A), or the therapeutic oligonucleotide region could base pair with some or even more than half of the second strand (FIGS. 4B-4F).

Considering just the first complementary region of the first strand, when composed of two or more types of nucleotides or nucleotide analogues, the bases can be arranged in a gapmer or a mixmer structure. For example, as a gapmer, the first complementary region may be arranged to have a center region comprising at least 4 consecutive RNA nucleotides, a first 5'-wing region, and a first 3'-wing region as described with respect to the sense strand in PCT/JP2012/083180, entitled "Chimeric Double-Stranded Nucleic Acid."

Considering just the therapeutic oligonucleotide region of the first strand, this region may comprise any type of nucleic acid therapeutic agent. Particular examples include antisense oligonucleotides, antagomir oligonucleotides, splice-switching oligonucleotides, single-stranded siRNA oligonucleotides, double-stranded siRNA oligonucleotides, microRNA, pre-microRNA, and aptamers. These agents can be prepared with any of the structures and designs known to those skilled in the art. For example, particular nucleotides or nucleotide analogs can be incorporated into the structure, or the arrangement of different types of bases into gapmer, mixmer, single wing, or double wing arrangements can be employed.

In some embodiments, the first complementary region is designed to be resistant to nuclease degradation, or more generally, metabolic degradation, when put into a biological sample (cell, tissue, animal, human, etc.). For example, the first complementary region may comprise bases (modified nucleotides or nucleotide analogues) that are more resistant to nuclease cleavage than natural bases, or it may comprise PNA. When the first complementary region is designed to be resistant to nuclease degradation, this region will generally remain connected to the therapeutic oligonucleotide in the methods disclosed herein. In this case, when reference is made to the release of the therapeutic oligonucleotide, it may be properly understood to mean the release of the first strand (the therapeutic oligonucleotide connected to the first complementary region).

In other embodiments, the first complementary region is designed to be susceptible to cleavage by RNase H when the first strand is hybridized to the second strand. Thus, at least a portion of the first complementary region and the second complementary region are designed to be recognized by RNase H when the two strands are annealed as a duplex. Generally, for this purpose the first strand comprises RNA nucleotides and the second strand comprises DNA nucleotides in order to form a heteroduplex. In some embodiments, the first complementary region comprises 2, 3, 4, or 5 or more consecutive natural RNA bases, which may optionally be flanked on one or both sides by modified RNA nucleotides. The portion of the second complementary region that is complementary to such first complementary region may comprise natural DNA, modified DNA, DNA analogues, or other such bases that promote the recognition of the heteroduplex structure and cleavage of the first strand.

In some embodiments, the therapeutic oligonucleotide region is designed to be resistant to nuclease degradation, or more generally, metabolic degradation, when put into a biological sample (cell, tissue, animal, human, etc.). For example, the therapeutic oligonucleotide region may comprise bases (modified nucleotides or nucleotide analogues) that are more resistant to nuclease cleavage than natural bases, or it may comprise PNA. In particular, the therapeutic oligonucleotide region is generally designed to have at least 1, 2, 3, or at least 4 bases at the 3' and the 5' terminal portion of the region that are more resistant to cleavage or degradation than natural bases. As noted above, some of these bases at one of the end portions may also be part of the first complementary region.

When the first complementary region contains some bases that are susceptible to cleavage or degradation, such as by RNase H, and a cleavage reaction occurs, the portion of the first strand that contains the therapeutic oligonucleotide region may still yet contain a part of the first complementary region. Some of these bases that were part of the first complementary region may be susceptible to further cleavage or degradation reactions. For example, such bases may be subject to cleavage by exonucleases. Even if such bases may be present they may be removed in the sample environment, but the presence of bases at the terminal portion of the therapeutic nucleotide region that are more resistant to cleavage or degradation than natural bases are expected to prevent the cleavage or degradation of the therapeutic oligonucleotide, such as by further action by exonucleases.

In still other embodiments, additional nucleotides or analogues may be included added at the 5' end, at the 3' end, or at both ends of either the first or second strands, and/or at either or both ends of the therapeutic oligonucleotide region, that display nuclease resistance and low binding affinity for proteins and protein-like cellular components.

The inventors have determined that the double-stranded nucleic acid agent, when introduced into a cell, can release the therapeutic oligonucleotide, which can then act, for example, to modify the activity or function of a transcription product. The transcription product may be a protein-encoding transcription product or a non-protein-encoding product such as miRNA. The application further contemplates methods for altering the expressed level of a protein in a cell, and for changing a protein structure by means of an antisense effect.

The double-stranded nucleic acid agent is also useful for treating patients having a condition characterized by an altered gene expression level, such that, for example, a protein is overexpressed. By treating the patient with a pharmaceutical composition comprising the double-stranded nucleic acid agent, the gene expression level can be specifically suppressed or inhibited to a degree that the protein levels decrease, thereby ameliorating the condition.

In certain embodiments, the following are provided.

(1) A method of delivering a therapeutic oligonucleotide to a cell comprising:

contacting with the cell a composition comprising:

a double-stranded nucleic acid agent comprising a first nucleic acid strand annealed to a second nucleic acid strand, wherein:

the first nucleic acid strand comprises (i) a first RNA region with at least 2 consecutive RNA nucleotides that can be recognized by RNase H when the first nucleic acid strand is hybridized to the second nucleic acid strand, (ii) a therapeutic oligonucleotide region wherein at least one internucleotide linkage at the 3' and at the 5' end of the therapeutic oligonucleotide region is more nuclease-resistant than a natural internucleotide linkage, and (iii) at least one internucleotide linkage at the 3' and at the 5' end of the first nucleic acid strand is more nuclease-resistant than a natural internucleotide linkage; the second nucleic acid strand comprises (i) a first DNA region that is hybridized to the first RNA region of the first nucleic acid strand and can promote the recognition of the at least 2 consecutive RNA nucleotides in the first nucleic acid strand by RNase H, and optionally (ii) at least one internucleotide linkage at the 3' and at the 5' end of the second nucleic acid strand is more nuclease-resistant than a natural internucleotide linkage; and the therapeutic oligonucleotide region of the first nucleic acid strand is not capable of hybridization with the second nucleic acid strand.

(2) The method according to item (1), wherein the first nucleic acid strand and the second nucleic acid strand comprise nucleotides selected from RNA nucleotides, DNA nucleotides, nucleotide analogs, and PNA nucleotides.

(3) The method according to item (1), wherein the first nucleic strand comprises nucleotides selected from DNA nucleotides, RNA nucleotides, nucleotide analogs, and PNA nucleotides, and the second nucleic acid strand comprises nucleotides selected from DNA nucleotides, nucleotide analogs, and PNA nucleotides.

(4) The method according to any one of items (1)-(3), wherein the therapeutic oligonucleotide region comprises an oligonucleotide selected from an antisense oligonucleotide, an antagomir oligonucleotide, a splice switching oligonucleotide, a single-stranded siRNA oligonucleotide, a double-stranded siRNA, a microRNA, a pre-microRNA, and an aptamer.

(5) The method according to item (4), wherein the antagomir oligonucleotide is a mixmer, is composed of one type of nucleotide or nucleotide analogue, or a gapmer.

(6) The method according to item (5), wherein antagomir comprises at least one nucleotide selected from 2'-OMe RNA, MOE, CET, ENA, LNA and AmNA, and at least one internucleotide linkage is optionally phosphorothioated.

(7) The method according to any one of items (1)-(6), wherein the second nucleic acid strand is a gapmer or a mixmer.

(8) The method according to any one of items (1)-(7), wherein the double-stranded nucleic acid agent further comprises a targeting moiety;
further wherein the targeting moiety is selected from a lipid, a sugar, a peptide, and a protein;
further wherein the lipid is selected from cholesterol, a tocopherol, a tocotrienol, a fatty acid, a lipid-soluble vitamin, a glycolipid, and a glyceride.

(9) The method according to item (8), wherein the targeting moiety is joined to the 3'-terminal nucleotide or the 5'-terminal nucleotide of the second nucleic acid strand, or to the 3'-terminal nucleotide or the 5'-terminal nucleotide of the first nucleic acid strand.

(10) The method according to any one of items (1)-(9), wherein the increased nuclease-resistance in the internucleotide linkages is due to at least one of a phosphorothioate group, a modified nucleotide, a nucleotide analogue, and a PNA nucleotide.

(11) The method according to any one of items (1)-(10), wherein the first nucleic acid strand comprises one or more nucleotides selected from modified RNA nucleotides and nucleotide analogs located 5' and located 3' to the at least 2 consecutive RNA nucleotides that can be recognized by RNase H.

(12) The method according to item (11), wherein the one or more nucleotides located 5' and located 3' to the at least 2 consecutive RNA nucleotides that can be recognized by RNase H are independently selected from LNA nucleotides, BNA nucleotides, 2'-O-Me RNA nucleotides, and 2'-O-methoxyethyl RNA nucleotides.

(13) The method according to item (11) or (12), wherein the one or more nucleotides located 5' and located 3' to the at least 2 consecutive RNA nucleotides that can be recognized by RNase H are independently optionally phosphorothioated.

(14) A method of delivering a therapeutic oligonucleotide to a cell comprising:
contacting with the cell a composition comprising:
a double-stranded nucleic acid agent comprising a first nucleic acid strand annealed to a second nucleic acid strand, wherein:
the first nucleic acid strand comprises (i) a first RNA region with at least 2 consecutive RNA nucleotides that can be recognized by RNase H when the first nucleic acid strand is hybridized to the second nucleic acid strand, (ii) one or more nucleotides selected from modified RNA nucleotides and nucleotide analogs located 5' and located 3' to the at least 2 consecutive RNA nucleotides that are recognized by RNase H, (iii) a therapeutic oligonucleotide region that comprises one or more nucleotides at the 3' and at the 5' end selected from modified RNA nucleotides and nucleotide analogs and which are independently optionally phosphorothioated, (iv) a targeting moiety selected from a lipid, a peptide, and a protein joined to either the 3'-terminal nucleotide or the 5'-terminal nucleotide and (v) the total number of nucleotides in the first nucleic acid strand is from 12 to 100;
the second nucleic acid strand comprises (i) a first DNA region that is hybridized to the first RNA region of the first nucleic acid strand and can promote the recognition of the at least 2 consecutive RNA nucleotides in the first nucleic acid strand by RNase H, and (ii) one or more nucleotides selected from modified DNA nucleotides and nucleotide analogs located 5' and located 3' to the first DNA region and which are independently optionally phosphorothioated; and
the therapeutic oligonucleotide region of the first nucleic acid strand is not capable of hybridization with the second nucleic acid strand.

(15) A method of delivering a therapeutic oligonucleotide to a cell comprising:
contacting with the cell a composition comprising:
a double-stranded nucleic acid agent comprising a first nucleic acid strand annealed to a second nucleic acid strand, wherein:
the first nucleic acid strand comprises (i) a first PNA region with at least 2 PNA nucleotides, (ii) a therapeutic oligonucleotide region wherein at least one internucleotide linkage at the 3' and at the 5' end of the therapeutic oligonucleotide region is more nuclease-resistant than a natural internucleotide linkage, and (iii) at least one internucleotide linkage at the 3' and at the 5' end of the first nucleic acid strand is more nuclease-resistant than a natural internucleotide linkage;
the second nucleic acid strand comprises (i) a first DNA region that is hybridized to the first PNA region of the first nucleic acid strand, and (ii) at least one internucleotide linkage at the 3' and at the 5' end of the second nucleic acid strand is more nuclease-resistant than a natural internucleotide linkage; and
the therapeutic oligonucleotide region of the first nucleic acid strand is not capable of hybridization with the second nucleic acid strand.

(16) A composition comprising:
a double-stranded nucleic acid agent comprising a first nucleic acid strand annealed to a second nucleic acid strand, wherein:
the first nucleic acid strand comprises (i) a first RNA region with at least 2 consecutive RNA nucleotides that can be recognized by RNase H when the first nucleic acid strand is hybridized to the second nucleic acid strand, (ii) a therapeutic oligonucleotide region wherein at least one internucleotide linkage at the 3' and at the 5' end of the therapeutic oligonucleotide region is more nuclease-resistant than a natural internucleotide linkage, (iii) at least one internucleotide linkage at the 3' and at the 5' end of the first nucleic acid strand is more nuclease-resistant than a natural internucleotide linkage, and (iv) the total number of nucleotides in the first nucleic acid strand is from 12 to 100;

the second nucleic acid strand comprises (i) a first DNA region that is hybridized to the first RNA region of the first nucleic acid strand and can promote the recognition of the at least 2 consecutive RNA nucleotides in the first nucleic acid strand by RNase H, (ii) optionally at least one internucleotide linkage at the 3' and at the 5' end of the second nucleic acid strand is more nuclease-resistant than a natural internucleotide linkage, and (iii) the total number of nucleotides in the second nucleic acid strand is at least 8; and the therapeutic oligonucleotide region of the first nucleic acid strand is not capable of hybridization with the second nucleic acid strand at in a mammalian cell at physiological temperature.

(17) A pharmaceutical composition comprising the double-stranded nucleic acid agent of item (16) and a pharmaceutically acceptable carrier.

(18) A method of reducing the expression level of a gene in a cell comprising the step of administering an effective amount to the cell of the composition of item (16) or (17).

(19) A method of modifying the function of a transcription product in a cell comprising the step of administering to the cell the composition of item (16) or (17).

(20) A method of changing the expressed level of a protein in a cell comprising the step of administering to the cell the composition of item (16) or (17).

(21) A method of changing a protein structure in a cell comprising the step of administering to the cell the composition of item (16) or (17).

(22) A method for treating a patient having a condition characterized by changing expression level, function or editing of a target gene, comprising:

administering to said patient a therapeutically effective amount of a pharmaceutical composition comprising (a) at least one double-stranded nucleic acid agent of item (16); and (b) a pharmaceutically acceptable carrier.

Certain embodiments include a purified or isolated double-stranded nucleic acid agent, comprising a first strand, which comprises a first complementary region and a therapeutic oligonucleotide region, and a second strand, which comprises a second complementary region, that is annealed to the first strand. In certain embodiments, such a double-stranded nucleic acid agent further comprises a targeting moiety.

According to certain embodiments, a double-stranded nucleic acid agent can be delivered to a target site with high specificity and high efficiency by associating a functional moiety, e.g., a delivery moiety, with the double-stranded complex.

Advantageous Effects of Invention

The double-stranded nucleic acid agent of the present invention can be delivered to a target site with high specificity and high efficiency, and the therapeutic oligonucleotide region included in the double-stranded nucleic acid exhibits splendid therapeutic effects at the target site.

BRIEF DESCRIPTION OF DRAWINGS

FIG. 1 is a diagram illustrating the general mechanisms of certain antisense methods. As illustrated in the diagram, when an oligonucleotide (antisense oligonucleotide (ASO)) ("DNA" in the diagram) that is complementary to a partial sequence of the mRNA of a target gene is introduced into a cell, the expression of a protein that is encoded by the target gene is selectively inhibited. In the dashed box, a degradation mechanism is shown in which RNase H cleaves mRNA at a location at which it is hybridized to an ASO. As a result of RNase H cleavage, the mRNA generally will not be translated to produce a functional gene expression product.

FIG. 2 is a schematic diagram illustrating the structures of RNA, DNA, and an LNA nucleotide.

FIGS. 3A-3B are schematic illustrations of suitable embodiments of double-stranded nucleic agents capable of delivering a therapeutic oligonucleotide. FIG. 4A shows the basic nucleotide framework, and FIG. 4B adds to that optional functional moieties "X," which may independently represent a lipid (for example, cholesterol or tocopherol), a sugar or the like, or a protein, a peptide (for example, an antibody) or the like, and which may serve as a targeting moiety.

FIGS. 4A-4F are schematic illustrations of various structures for a first strand and a second strand, and the relationship of the therapeutic oligonucleotide portion of the first strand to the complementary regions of the first and second strands.

FIGS. 5A-5D are schematic diagrams illustrating a mechanism by which the therapeutic oligonucleotide may be released from the double-stranded nucleic acid agent.

FIG. 6 shows the structural formula of various natural and modified nucleic acid or nucleic acid analogue moieties.

FIGS. 7-1A to 7-1C are schematic illustrations of the structures of the double-stranded nucleic acid agents used in the Example 1.

FIGS. 7-2D to 7-2E shows the Northern blot analyses of the experiments of Example 1.

FIG. 8 shows in the upper portion of the figure the sequence and composition of the oligonucleotides used in Example 2, and shows in the lower portion a graph of the results of Example 2, in which the in vivo suppression of microRNA 122 (miR122) in mice by the double-stranded nucleic acid agent was tested.

FIG. 9 shows the sequence and composition of the oligonucleotides used in Example 3.

FIG. 10a shows a graph of the results of Example 3, in which the in vivo suppression of microRNA 122 (miR122) was tested.

FIG. 10b shows a graph of the results of Example 3, in which expression of aldolase A (ALDOA) in mice by the double-stranded nucleic acid agent was tested.

FIG. 10c shows a graph of the results of Example 3, in which expression of branched chain ketoacid dehydrogenase kinase (BCKDK) in mice by the double-stranded nucleic acid agent was tested.

FIG. 10d shows a graph of the results of Example 3, in which serum total cholesterol level (FIG. 10d) in mice by the double-stranded nucleic acid agent was tested.

FIG. 10e shows a graph of the results of Example 3, in which serum LDL level in mice by the double-stranded nucleic acid agent was tested.

FIG. 10f shows the dose-dependent phenotype effect for serum total cholesterol level.

FIG. 11 shows the sequence and composition of the oligonucleotides used in Example 4.

FIG. 12 shows a graph of the results of Example 4 comparing the exon-skipping effect of double-stranded nucleic acid with that of single-stranded nucleic acid.

FIG. 13 shows the sequence and composition of the oligonucleotides used in Example 5.

FIG. 14 shows a graph of the results of Example 5 demonstrating the inhibition of the expression of ApoB mRNA by targeting intron of pre-mRNA of ApoB with double-stranded nucleic acid.

FIG. 15 shows the sequence and composition of the oligonucleotides used in Example 6.

FIG. 16 shows a graph of the results of Example 6 comparing the inhibition in the expression of miR122 by double-stranded nucleic acid with that by single-stranded nucleic acid.

FIG. 17 shows the sequence and composition of the oligonucleotides used in Example 7.

FIG. 18 shows a graph of the results of Example 7 demonstrating the inhibition of the expression of ApoB mRNA by targeting intron of pre-mRNA of ApoB with double-stranded nucleic acid.

FIG. 19 shows the sequence and composition of the oligonucleotides used in Example 8.

FIG. 20 shows a graph of the results of Example 8 demonstrating the inhibition of the expression of ApoB mRNA by targeting intron of pre-mRNA of ApoB with double-stranded nucleic acid.

FIG. 21 shows the sequence and composition of the oligonucleotides used in Example 9.

FIG. 22 shows a graph of the results of Example 8 demonstrating the therapeutic effects of antimiR-3' and antimiR-5'.

DESCRIPTION OF EMBODIMENTS

The "antisense effect" means suppressing the expression of a target gene or the level of a targeted transcription product, which occurs as a result of hybridization of the targeted transcription product (RNA sense strand) with, for example, a DNA strand, or more generally, a strand designed to cause the antisense effect, complementary to a partial sequence of the transcription product or the like. In certain instances, inhibition of translation or a splicing function modifying effect such as exon skipping (see the description in the upper part outside the area surrounded by dotted lines in FIG. 1) may be caused by covering of the transcription product by the hybridization product, and/or decomposition of the transcription product may occur as a result of recognition of the hybridized portion (see the description within the area surrounded by dotted lines in FIG. 1). Further, in certain instances, the antisense effect is brought by targeting intron of pre-mRNA.

The antisense effect is possessed by a therapeutic oligonucleotide portion of the double-strand agent for delivering therapeutic polynucleotide of the present invention. The antisense effect may be possessed by a first nucleic acid strand. In this case, the therapeutic effect is increased synergistically by the oligonucleotide portion and the first nucleic acid strand.

The "target gene" or "targeted transcription product" whose expression is suppressed by the antisense effect is not particularly limited, and examples thereof include genes whose expression is increased in various diseases. Also, the "transcription product of the target gene" is an mRNA transcribed from the genomic DNA that encodes the target gene, and also includes an mRNA that has not been subjected to base modification, an mRNA precursor that has not been spliced, and the like. More generally, the "transcription product" may be any RNA synthesized by a DNA-dependent RNA polymerase.

As used herein, the term "nucleic acid" may refer to a monomeric nucleotide or nucleoside, or may mean an oligonucleotide consisting of plural monomers. The term "polynucleotide" and "nucleic acid strand" is also used herein to refer to an oligonucleotide. Nucleic acid strands may be prepared in whole or in part by chemical synthesis methods, including using an automated synthesizer or by enzymatic processes, including but not limited to polymerase, ligase, or restriction reactions.

The term "complementary" as used herein means a relationship in which so-called Watson-Crick base pairs (natural type base pair) or non-Watson-Crick base pairs (Hoogsteen base pairs and the like) can be formed via hydrogen bonding. It is not necessary that the base sequence of (a) the first complementary region and the second complementary region, or (b) the targeted transcription product, e.g., the transcription product of a target gene, and the base sequence of the therapeutic oligonucleotide, be perfectly complementary, and it is acceptable if the base sequences have a complementarity of at least 70% or higher, preferably 80% or higher, and more preferably 90% or higher (for example, 95%, 96%, 97%, 98%, or 99% or higher). The complementarity of sequences can be determined by using a BLAST program or the like. A first strand can be "annealed" or "hybridized" to a second strand when the sequences are complementary. A person of ordinary skill in the art can readily determine the conditions (temperature, salt concentration, etc.) under which two strands can be annealed, taking into account the degree of complementarity between the strands. Also, a person having ordinary skill in the art can readily design first and second complementary regions, and a therapeutic oligonucleotide complementary to the targeted transcription product based on the information of the base sequence of, e.g., the target gene.

The length of the first or second complementary regions or the therapeutic oligonucleotide region is not particularly limited, but the length of either region is usually at least 8 bases, at least 10 bases, at least 12 bases, or at least 13 bases. The length of either region may be up to 20 bases, 25 bases, or 35 bases, or more. The total length of the first strand may even be as long as about 100 bases. In some embodiments, ranges of the length of the second strand may be 10 to 35 bases, 12 to 25 bases, or 13 to 20 bases.

The choice of the length of the first or second complementary regions depends on the balance of the binding affinity of each opposing base, the degree of complementarity, and the temperature of biological sample with which the double-stranded nucleic acid agent is to be contacted. The length of the portion of the first and second complementary regions that bind to one another should be long enough such that the thermodynamic stability of the annealed strands favors the two strands remaining substantially bound to one another during the time that the agent is contacted with a biological sample. Other factors, such as proteins, enzymes, or other cellular components may cause the strands to separate or unwind.

In some embodiments the therapeutic oligonucleotide region contains some bases that bind with the second complementary region in the annealed double-stranded agent. The choice of length of this "overlapping region" depends on the temperature of the biological sample with which the agent is to be contacted. Generally, the therapeutic oligonucleotide region of the first strand is not capable of hybridization with the second strand at the temperature of operation. The temperature of operation may be an incubation temperature or the physiological body temperature of the subject or patient.

The choice of length of the therapeutic oligonucleotide generally depends on a balance of the strength of the antisense effect with the specificity of the nucleic acid sequence for the target, among other factors such as cost, synthetic yield, and the like.

In some embodiments, the choice of the length of the therapeutic oligonucleotide and the degree of complementarity between it and the targeted transcription product may also depend on the binding affinity between the therapeutic oligonucleotide and the target after the target has been cleaved by RNase H. The potency of a therapeutic oligonucleotide depends both on the binding affinity of the therapeutic oligonucleotide with the target prior to cleavage as well as the off-rate for the cleaved material to dissociate from the therapeutic oligonucleotide so it is freed to bind to another target strand.

The first and second complementary regions may comprise natural and/or non-natural nucleotides. The type of nucleotides selected for the complementary regions largely determines the type of mechanism(s) by which the therapeutic oligonucleotide may be released. For example, including RNA and/or RNA-like nucleotides in the first strand and DNA and/or DNA-like nucleotides in the second strand leads to the formation of DNA/RNA heteroduplex structures that can be recognized by RNase H. Thus, RNase H-dependent mechanism of action is possible in this case, in which case the first strand can be cleaved by RNase H.

Such a process is illustrated in FIG. 5A-5D. FIG. 5A shows an annealed duplex formed between (i) a first strand (bottom strand in the figure) that contains a 2'-OMe RNA/RNA gapmer-type first complementary region and a 2'-OMe RNA antagomir-type therapeutic oligonucleotide and (ii) a second strand (upper strand in the figure) that has an LNA/DNA gapmer-type second complementary region. The first strand also contains a cholesterol moiety that can deliver the double-stranded agent to, e.g., the liver. Once the agent is delivered, e.g., to the liver, and enters a cell, as shown in FIG. 5B, RNase H recognizes the DNA/RNA heteroduplex and cleaves the RNA sequence in the first strand. This separates the therapeutic oligonucleotide from the targeting moiety, and leaves very few bases to bind the cut first strand to the second strand. And, it exposes some RNA bases at the end of the now-cleaved first strand. FIG. 5C illustrates that cleaved first strand separates from the second strand to become a free single-stranded oligonucleotide and, the exposed RNA bases are subject to cleavage by an exonuclease. As illustrated in FIG. 5D, the exonuclease activity can trim the released strand down to just the therapeutic oligonucleotide region, and thus the double-stranded agent can serve to deliver a therapeutic oligonucleotide within a biological sample.

On the other hand, if DNA and/or DNA-like nucleotides are excluded from the second complementary region, then RNase H-independent mechanisms of action are expected to occur. Of course, even if DNA/RNA heteroduplex structures are formed, RNase H-independent mechanisms may occur.

In some embodiments, the second complementary region comprises at least 5 nucleotides that when hybridized to an RNA polynucleotide, the first/second complementary region duplex is recognized by RNase H.

The "at least 5 nucleotides" that when hybridized to RNA are "recognized by RNase H" is usually a region comprising 5 to 20 consecutive bases, a region comprising 5 to 16 consecutive bases, a region comprising 5 to 12 consecutive bases, or a region comprising 5 to 8 consecutive bases. Furthermore, nucleotides that may be used in this region are those that, like natural DNA, are recognized by RNase H when hybridized to RNA nucleotides, wherein the RNase H cleaves the RNA strand. Suitable nucleotides, such as modified DNA nucleotides and other bases are known in the art. In some embodiments, natural DNA and modified DNA nucleotides can be mixed in a mixmer-type arrangement and still induce RNase H activity. Nucleotides that contain a 2'-hydroxy group, like an RNA nucleotide are known to not be suitable. One of skill in the art can readily determine the suitability of a nucleotide for use in this region of "at least 5 nucleotides" when an RNase H-dependent effect is desired. In one embodiment, the nucleotides of the complementary region are independently selected from DNA and phosphorothioate DNA nucleotides.

In some embodiments, the second complementary region may comprise as few as 4 nucleotides that when hybridized to an RNA polynucleotide, the center nucleotide region/RNA polynucleotide duplex is recognized and cleaved by RNase H.

In some embodiments, the first complementary region may have 2, 3, 4, or 5, or more consecutive natural RNA nucleotides, and this subsequence can be cleaved by RNase H in a suitable heteroduplex structure.

As used herein, "DNA nucleotide" means a natural DNA nucleotide, or a DNA nucleotide with a modified base, sugar, or phosphate linkage subunit. Similarly, "RNA nucleotide" means a natural RNA nucleotide, or an RNA nucleotide with a modified base, sugar, or phosphate linkage subunit. A modified base, sugar, or phosphate linkage subunit is one in which a single substituent has been added or substituted in a subunit, and the subunit as a whole has not been replaced with a different chemical group. From the viewpoint that a portion or the entirety of the nucleic acid strands have high resistance to deoxyribonuclease and the like, the DNA may be a modified nucleotide. Examples of such modification include 5-methylation, 5-fluorination, 5-bromination, 5-iodination, and N4-methylation of cytosine; 5-demethylation, 5-fluorination, 5-bromination, and 5-iodination of thymidine; N6-methylation and 8-bromination of adenine; N2-methylation and 8-bromination of guanine; phosphorothioation, methylphosphonation, methylthiophosphonation, chiral methylphosphonation, phosphorodithioation, phosphoroamidation, 2'-O-methylation, 2'-methoxyethyl(MOE)ation, 2'-aminopropyl(AP)ation, and 2'-fluorination. However, from the viewpoint of having excellent pharmacokinetics, phosphorothioation is preferred. Such modification may be carried out such that the same DNA may be subjected to plural kinds of modifications in combination. And, as discussed below, RNA nucleotides may be modified to achieve a similar effect.

In certain instances, the number of modified DNA's or RNA's and the position of modification may affect the antisense effect and the like provided by the therapeutic oligonucleotide or the release of the therapeutic oligonucleotide as disclosed herein. Since these embodiments may vary with the sequence of the complement and the like, it may depend on the circumstances, but a person having ordinary skill in the art can determine suitable embodiments by referring to the descriptions of documents related to antisense methods. Furthermore, when the antisense effect possessed by a therapeutic oligonucleotide or the release of the therapeutic oligonucleotide after modification is measured, if the measured value thus obtained is not significantly lower than the measured value of the therapeutic oligonucleotide before modification (for example, if the measured value obtained after modification is lower by 30% or more than the measured value of the therapeutic oligonucleotide before modification), the relevant modification can be evaluated. The measurement of the antisense effect can be carried out, as indicated in the Examples below, by introducing a candidate double-stranded agent under test into a cell or the like, and measuring the amount of expression (amount of mRNA, amount of cDNA, amount of a protein, amount of microRNA, or the like) of the targeted transcription product in the cell in which the expression is suppressed by the antisense effect provided by the candidate agent under test, by appropriately using known techniques such as Northern Blotting, quantitative PCR, and Western Blotting. The candidate agent may be the therapeutic oligonucleotide itself, or as part of a double-stranded nucleic acid agent.

As used herein, "RNA nucleotide" means a naturally occurring RNA nucleotide, or an RNA nucleotide with a modified base, sugar, or phosphate linkage subunit. A modified base, sugar, or phosphate linkage subunit is one in which a single substituent has been added or substituted in a subunit, and the subunit as a whole has not been replaced with a different chemical group.

A portion or the entirety of the nucleic acid strands may be a modified nucleotide, from the viewpoint of having high resistance to a nuclease such as a ribonuclease (RNase). Examples of such modification include 5-methylation, 5-fluorination, 5-bromination, 5-iodination and N4-methylation of cytosine; 5-demethylation, 5-fluorination, 5-bromination, and 5-iodination of thymidine; N6-methylation and 8-bromination of adenine; N2-methylation and 8-bromination of guanine; phosphorothioation, methylphosphonation, methylthiophosphonation, chiral methylphosphonation, phosphorodithioation, phosphoroamidation, 2'-O-methylation, 2'-methoxyethyl(MOE)ation, 2'-aminopropyl(AP) lation, and 2'-fluorination. Also, an RNA nucleotide with a thymidine base substituted for a uracil base is also contemplated. However, from the viewpoint of having excellent pharmacokinetics, phosphorothioation is used. Furthermore, such modification may be carried out such that the same nucleic acid may be subjected to plural kinds of modifications in combination. For example, as used in the Examples described below, the same RNA may be subjected to phosphorothioation and 2'-O-methylation in order to provide resistance to enzymatic cleavage. However, where it is expected or desired for an RNA nucleotide to be cleaved by RNase H, then only either phosphorothioation or 2'-O-methylation is generally applied.

As used herein, "nucleotide analog" means a non-naturally occurring nucleotide, wherein the base, sugar, or phosphate linkage subunit has more than one substituent added or substituted in a subunit, or that the subunit as a whole has been replaced with a different chemical group. An example of an analog with more than one substitution is a bridged nucleic acid, wherein a bridging unit has been added by virtue of two substitutions on the sugar ring, typically linked to the 2' and 4' carbon atoms. In regard to certain embodiments, from the viewpoint of increasing the affinity to a partial sequence of the targeted transcription product and/or the resistance of the strand to a nuclease, the antisense polynucleotide strand further comprises a nucleotide analog. The "nucleotide analog" may be any nucleic acid in which, owing to the modifications (bridging groups, substituents, etc.), the affinity to a partial sequence of the complement or the targeted transcription product and/or the resistance of the nucleic acid to a nuclease is enhanced, and examples thereof include nucleic acids that are disclosed to be suitable for use in antisense methods, in JP 10-304889 A, WO 2005/021570, JP 10-195098 A, JP 2002-521310 W, WO 2007/143315, WO 2008/043753, WO 2008/029619, and WO 2008/049085 (hereinafter, these documents will be referred to as "documents related to antisense methods"). That is, examples thereof include the nucleic acids disclosed in the documents described above: a hexitol nucleic acid (HNA), a cyclohexane nucleic acid (CeNA), a peptide nucleic acid (PNA), a glycol nucleic acid (GNA), a threose nucleic acid (TNA), a morpholino nucleic acid, a tricyclo-DNA (tcDNA), a 2'-O-methylated nucleic acid, a 2'-MOE (2'-O-methoxyethyl)lated nucleic acid, a 2'-AP (2'-O-aminopropyl)lated nucleic acid, a 2'-fluorinated nucleic acid, a 2'-F-arabinonucleic acid (2'-F-ANA), and a BNA (bridged nucleic acid).

The BNA according to certain embodiments may be any ribonucleotide or deoxyribonucleotide in which the 2' carbon atom and 4' carbon atom are bridged by two or more atoms. Examples of bridged nucleic acids are known to those of skill in the art. One subgroup of such BNA's can be described as having the carbon atom at the 2'-position and the carbon atom at the 4'-position bridged by 4'-$(CH_2)_p$—O-2',4'-$(CH_2)_p$—S-2',4'-$(CH_2)_p$—OCO-2',4'-$(CH_2)_n$—N($R_3$)—O—$(CH_2)_m$-2' (here, p, m and n represent an integer from 1 to 4, an integer from 0 to 2, and an integer from 1 to 3, respectively; and $R_3$ represents a hydrogen atom, an alkyl group, an alkenyl group, a cycloalkyl group, an aryl group, an aralkyl group, an acyl group, a sulfonyl group, and a unit substituent (a fluorescent or chemiluminescent labeling molecule, a functional group having nucleic acid cleavage activity, an intracellular or intranuclear localization signal peptide, or the like)). Furthermore, in regard to the BNA according certain embodiments, in the $OR_2$ substituent on the carbon atom at the 3'-position and the $OR_1$ substituent on the carbon atom at the 5'-position, $R_1$ and $R_2$ are typically hydrogen atoms, but may be identical with or different from each other, and may also be a protective group of a hydroxyl group for nucleic acid synthesis, an alkyl group, an alkenyl group, a cycloalkyl group, an aryl group, an aralkyl group, an acyl group, a sulfonyl group, a silyl group, a phosphoric acid group, a phosphoric acid group protected by a protective group for nucleic acid synthesis, or —P($R_4$)$R_5$ (here, $R_4$ and $R_5$, which may be identical with or different from each other, each represent a hydroxyl group, a hydroxyl group protected by a protective group for nucleic acid synthesis, a mercapto group, a mercapto group protected by a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted with an alkyl group having 1 to 5 carbon atoms). Non-limiting examples of such a BNA include alpha-L-methyleneoxy(4'-$CH_2$—O-2')BNA or beta-D-methyleneoxy(4'-$CH_2$—O-2')BNA, which are also known as LNA (Locked Nucleic Acid (registered trademark), 2',4'-BNA), ethyleneoxy(4'-$(CH_2)_2$—O-2')BNA which is also known as ENA, beta-D-thio(4'-$CH_2$—S-2')BNA, aminooxy(4'-$CH_2$—O—N($R_3$)-2')BNA, oxyamino(4'-$CH_2$—N($R_3$)—O-2')BNA which is also known as 2',4'-BNA$^{NC}$, 2',4'-BNA$^{COC}$, 3'-amino-2',4'-BNA, 5'-methyl BNA, (4'-CH($CH_3$)—O-2')BNA, which is also known as cEt BNA, (4'-CH($CH_2OCH_3$)—O-2')BNA, which is also known as cMOE BNA, amideBNA (4'-C(O)—N(R)—2')BNA (R=H, Me), which is also known as AmNA, and other BNA's known to those of skill in the art.

Furthermore, in the nucleotide analog, according to certain embodiments, a base moiety may be modified. Examples of the modification at a base moiety include 5-methylation, 5-fluorination, 5-bromination, 5-iodination, and N4-methylation of cytosine; 5-demethylation, 5-fluorination, 5-bromination, and 5-iodination of thymidine; N6-methylation and 8-bromination of adenine; and N2-methylation and 8-bromination of guanine. Furthermore, in the modified nucleic acid according to certain embodiments, a phosphoric acid diester binding site may be modified. Examples of the modification of the phosphoric acid diester binding site include phosphorothioation, methylphosphonation, methylthiophosphonation, chiral methylphosphonation, phosphorodithioation, and phosphoroamidation. However, from the viewpoint of having excellent pharmacokinetics, phosphorothioation may be used. Also, such modification of a base moiety or modification of a phosphoric acid diester binding site may be carried out such that the same nucleic acid may be subjected to plural kinds of modifications in combination.

Generally, modified nucleotides and modified nucleotide analogs are not limited to those exemplified herein. Numerous modified nucleotides and modified nucleotide analogs are known in art, such as, for example those disclosed in U.S. Pat. No. 8,299,039 to Tachas et al., particularly at col. 17-22, and may be used in the embodiments of this application. Examples of a natural nucleotides, modified nucleotides, and nucleotide analogs are shown in FIG. 6.

A person having ordinary skill in the art can appropriately select and use a nucleotide analog among such modified nucleic acids while taking consideration of the antisense effect, affinity to a partial sequence of the transcription product of the target gene, resistance to a nuclease, and the like. However, the nucleotide analog in some embodiments is a LNA represented by the following formula (1):

[Chem. 1]

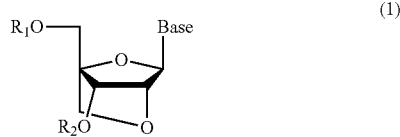

(1)

In formula (1), "Base" represents an aromatic heterocyclic group or aromatic hydrocarbon ring group which may be substituted, for example, a base moiety (purine base or pyrimidine base) of a natural nucleoside, or a base moiety of a non-natural (modified) nucleoside, while examples of modification of the base moiety include those described above; and $R_1$ and $R_2$, which may be identical with or different from each other, each represent a hydrogen atom, a protective group of a hydroxyl group for nucleic acid synthesis, an alkyl group, an alkenyl group, a cycloalkyl group, an aryl group, an aralkyl group, an acyl group, a sulfonyl group, a silyl group, a phosphoric acid group, a phosphoric acid group protected by a protective group for nucleic acid synthesis, or —$P(R_4)R_5$ {here, $R_4$ and $R_5$, which may be identical or different from each other, each represent a hydroxyl group, a hydroxyl group protected by a protective group for nucleic acid synthesis, a mercapto group, a mercapto group protected by a protective group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted with an alkyl group having 1 to 5 carbon atoms.

The compounds shown by the above chemical formulas are represented as nucleosides, but the "LNA" and more generally, the BNA according to certain embodiments include nucleotide forms in which a phosphoric acid derived group is bound to the relevant nucleoside (nucleotide). In other words, BNA's, such as LNA, are incorporated as nucleotides in the nucleic strands that comprise the double stranded nucleic acid complex.

A "low protein-affinity nucleotide" is a nucleotide that is (i) more resistant to DNase or RNase than a natural DNA or RNA nucleotide and (ii) possesses low affinity for binding to protein or protein-like cellular components. In particular, the nucleotide has a lower binding affinity towards proteins than a phosphorothioated nucleotide. Accordingly, a low protein-affinity nucleotide is a modified nucleotide or a nucleotide analog as described above, but the nucleotide is not phosphorothioated.

Examples of low protein-affinity nucleotides include 2'-O-methyl RNA nucleotides, 2'-O-methoxyethyl RNA nucleotides, LNA, cMOE BNA, 2-fluoro RNA nucleotides, boranophosphate nucleotides, methylphosphonate nucleotides, phosphoramidite nucleotides, 5-methylcytosine, and 5-propynyluridine.

When the double-stranded nucleic acid agent of certain embodiments is recognized by RNase H in the cell and the first nucleic acid strand is cleaved, releasing the therapeutic oligonucleotide, the second strand is released unchanged into solution. In some embodiments, the second strand may itself have antisense activity.

In some embodiments, the double-stranded nucleic acid agent comprises more than two polynucleotide strands. For example, two first strands may form a double-stranded complex with one second strand. Each first strand may comprise the same therapeutic oligonucleotide region, or have different therapeutic oligonucleotides that would act on the same or different targeted transcription product. Other multistrand constructs for delivery of multiple therapeutic oligonucleotides can be prepared in view of the description provided herein.

In the double-stranded nucleic acid agent, one or more of the constituent polynucleotides may further comprise a functional moiety.

In some embodiments, the first or second strand may comprise a functional moiety bonded to the polynucleotide. Referring back to FIG. 3B, a functional moiety "X" is illustrated joined to the terminal positions of the two strands. The functional moiety, further described below, could be joined to some or all of these ends, or at a position internal to the polynucleotides. In other embodiments, the complementary strand comprises more than one functional moiety, which may be joined at a plurality of positions, and/or joined as a group to one position of the polynucleotide.

The bonding between the polynucleotide (e.g., first strand or second strand) and the functional moiety may be direct bonding, or may be indirect bonding mediated by another material. However, in certain embodiments, it is preferable that a functional moiety be directly bonded to the polynucleotide via covalent bonding, ionic bonding, hydrogen bonding or the like, and from the viewpoint that more stable bonding may be obtained, covalent bonding is more preferred. The functional moiety may also be bonded to the polynucleotide via a cleavable linking group. For example, the functional moiety may be linked via a disulfide bond.

There are no particular limitations on the structure of the "functional moiety" according to certain embodiments, provided it imparts the desired function to the chimeric polynucleotide. The desired functions include a labeling function, a purification function, and a delivery function. Examples of moieties that provide a labeling function include compounds such as fluorescent proteins, luciferase, and the like. Examples of moieties that provide a purification function include compounds such as biotin, avidin, a His tag peptide, a GST tag peptide, a FLAG tag peptide, and the like.

Furthermore, from the viewpoint of delivering the double-stranded agent to a target site with high specificity and high efficiency, and thereby suppressing very effectively the expression of a target gene by the relevant nucleic acid, it is preferable that a molecule having an activity of delivering the double-stranded agent of some embodiments to a "target site" within the body, be bonded as a functional moiety to the first strand. In some embodiments, it is preferred that the functional moiety is joined to the first at the terminal that is closest to the first complementary region, that is, the terminal more distant from the therapeutic oligonucleotide region.

The moiety having a "targeted delivery function" may be, for example, a lipid, from the viewpoint of being capable of delivering the double-stranded agent of certain embodiments to the liver or the like with high specificity and high efficiency. Examples of such a lipid include lipids such as cholesterol and fatty acids (for example, vitamin E (tocopherols, tocotrienols), vitamin A, and vitamin D); lipid-soluble vitamins such as vitamin K (for example, acylcarnitine); intermediate metabolites such as acyl-CoA; glycolipids, glycerides, and derivatives thereof. However, among these, from the viewpoint of having higher safety, in certain embodiments, cholesterol and vitamin E (tocopherols and tocotrienols) are used. Furthermore, from the viewpoint of being capable of delivering the double-stranded agent of certain embodiments to the brain with high specificity and high efficiency, examples of the "functional moiety" according to the certain embodiments include sugars (for example, glucose and sucrose). Also, from the viewpoint of being capable of delivering the double-stranded agent of certain embodiments to various organs with high specificity and high efficiency by binding to the various proteins present on the cell surface of the various organs, examples of the "functional moiety" according to certain embodiments include peptides or proteins such as receptor ligands and antibodies and/or fragments thereof.

Techniques for coupling labels to a nucleic acid strand vary with the nature of the labeling moiety and the point of attachment in the nucleic acid, and these are well-known in the art. Although not illustrated, functional moieties may be joined to the polynucleotide at internal sites and not at the strand terminal sites. Again, such techniques are well-known in the art.

Thus, some suitable exemplary embodiments of the double-stranded agent of some embodiments have been described, but the double-stranded agent is not intended to be limited to the exemplary embodiments described above. Furthermore, any person having ordinary skill in the art can produce the polynucleotides that make up the double-stranded nucleic acid agent according to the various embodiments by appropriately selecting a known method. For example, the nucleic acids according to some embodiments can be produced by designing the respective base sequences of the nucleic acids on the basis of the information of the base sequence of the targeted transcription product (or, in some cases, the base sequence of a targeted gene), synthesizing the nucleic acids by using a commercially available automated nucleic acid synthesizer (products of Applied Biosystems, Inc.; products of Beckman Coulter, Inc.; and the like), and subsequently purifying the resulting oligonucleotides by using a reverse phase column or the like. Nucleic acids produced in this manner are mixed in an appropriate buffer solution and denatured at about 90 degrees C. to 98 degrees C. for several minutes (for example, for 5 minutes), subsequently the nucleic acids are annealed at about 30 degrees C. to 70 degrees C. for about 1 to 8 hours, and thus the double-stranded nucleic acid agent of some embodiments can be produced. Furthermore, a polynucleotide bearing a functional moiety can be produced by joining a functional moiety to the oligonucleotide strand during or after the oligonucleotide synthesis. Numerous methods for joining functional moieties to nucleic acids are well-known in the art.

Thus, suitable exemplary embodiments of the first strand and the second strand have been described. Additional embodiments are also disclosed in the following Examples. However, the double-stranded agent as contemplated by the inventors is not limited to the exemplary embodiments described above, or in the Examples below.

Compositions for modifying the expression of target gene or level of targeted transcription product by means of antisense effect are also contemplated.

The double-stranded nucleic acid agent of some embodiments can be delivered to a target site with high specificity and high efficiency and can very effectively suppress the expression of a target gene or the level of a transcription product, as will be disclosed in the Examples described below. Therefore, some embodiments provide a composition that contains the double-stranded antisense agent of some embodiments as an active ingredient and is intended to modify or suppress, e.g., the expression of a target gene or the activity of a microRNA by means of an antisense effect. Particularly, the double-stranded agent of some embodiments can give high efficacy even when administered at a low concentration, and the design also displays reduced toxicity. Further, by directing the double-stranded agent to particular organs, adverse side effects can be reduced. Therefore, some embodiments can also provide a pharmaceutical composition intended to treat and prevent diseases that are associated with, e.g., increased expression of a target gene, such as metabolic diseases, tumors, and infections.

The composition containing the double-stranded agent of some embodiments can be formulated by known pharmaceutical methods. For example, the composition can be used enterally (perorally or the like) in the form of capsules, tablets, pills, liquids, powders, granules, fine granules, film-coating agents, pellets, troches, sublingual agents, peptizers, buccal preparations, pastes, syrups, suspensions, elixirs, emulsions, coating agents, ointments, plasters, cataplasms, transdermal preparations, lotions, inhalers, aerosols, injections and suppositories, or non-enterally.

In regard to the formulation of these preparations, pharmacologically acceptable carriers or carriers acceptable as food and drink, specifically sterilized water, physiological saline, vegetable oils, solvents, bases, emulsifiers, suspending agents, surfactants, pH adjusting agents, stabilizers, flavors, fragrances, excipients, vehicles, antiseptics, binders, diluents, isotonizing agents, soothing agents, extending agents, disintegrants, buffering agents, coating agents, lubricating agents, colorants, sweetening agents, thickening agents, corrigents, dissolution aids, and other additives can be appropriately incorporated.

On the occasion of formulation, as disclosed in Non-Patent Document 2, the double-stranded agent of some embodiments to which a lipid is bound as a functional moiety may be caused to form a complex with a lipoprotein, such as chylomicron or chylomicron remnant. Furthermore, from the viewpoint of increasing the efficiency of enteral administration, complexes (mixed micelles and emulsions) with substances having a colonic mucosal epithelial permeability enhancing action (for example, medium-chain fatty acids, long-chain unsaturated fatty acids, or derivatives thereof (salts, ester forms or ether forms)) and surfactants (nonionic surfactants and anionic surfactants) may also be used, in addition to the lipoproteins.

There are no particular limitations on the preferred form of administration of the composition of some embodiments, and examples thereof include enteral (peroral or the like) or non-enteral administration, more specifically, intravenous administration, intraarterial administration, intraperitoneal administration, subcutaneous administration, intracutaneous administration, tracheobronchial administration, rectal administration, and intramuscular administration, and administration by transfusion.

The composition of some embodiments can be used for animals including human beings as subjects. However, there are no particular limitations on the animals excluding human beings, and various domestic animals, domestic fowls, pets, experimental animals and the like can be the subjects of some embodiments.

When the composition of some embodiments is administered or ingested, the amount of administration or the amount of ingestion may be appropriately selected in accordance with the age, body weight, symptoms and health condition of the subject, type of the composition (pharmaceutical product, food and drink, or the like), and the like. However, the effective amount of ingestion of the composition according to the certain embodiments is 0.001 mg/kg/day to 50 mg/kg/day of the therapeutic oligonucleotide.

The double-stranded agent of some embodiments can be delivered to a target site with high specificity and high efficiency, and can modify or suppress the expression of a target gene or the level of a transcription product very effectively, as will be disclosed in the Examples that follow. Therefore, some embodiments can provide a method of administering the double-stranded agent of some embodiments to a subject, and suppressing the expression of a target gene or transcription product level by means of an antisense effect. Furthermore, a method of treating or preventing various diseases that are associated with, e.g., increased expression of target genes, by administering the composition of some embodiments to a subject can also be provided.

EXAMPLES

Hereinafter, some embodiments will be described more specifically by way of Examples and Comparative Examples, but the embodiments not intended to be limited to the following Examples.

Example 1

An in vivo experiment demonstrating the utility of a gapmer or a mixmer-type structure for the second strand in a double-stranded nucleic agent according to an embodiment was conducted. The structures of the double-stranded agents and the results of the experiment are shown in FIGS. 7-1 and 7-2.

The first strand comprised an RNA-based complementary region with a gapmer-like structure and a therapeutic oligonucleotide that was a partially phosphorothioated, 2'-OMe RNA antagomir. The first strand also had a tocopherol group joined at the 5'-terminal position as a targeting moiety, to deliver the double-stranded agent to the liver. The first strand is schematically illustrated in FIGS. 7A and 7B. In addition, as a control, a first strand comprised entirely of 2'-OMe RNA nucleotides was similarly prepared. By replacing the RNA nucleotides with 2'-OMe RNA nucleotides, the RNA-based complementary region is expected to be resistant to cleavage by RNase H.

The second strand was 13-mer gapmer-type (FIG. 7-1A, 7-1C) or a mixmer-type (FIG. 7-1B) LNA/DNA oligonucleotide. Each internucleotide position was phosphorothioated. The gapmer had an 8 base central region of DNA bases that are fully complementary to the first strand sequence. The mixmer had three-base, two-base, and three-base runs of DNA separated by LNA bases as illustrated. The second strand is complementary to mouse apoB mRNA (NM_009693).

The sequence, composition, and strand length of the first and second strands were as follows:

```
First strand
31 mer Toc-cRNA-G
                                        (SEQ ID NO: 1)
5'-Toc-u*g*a*AUACCAAUg*c*uacgcauacgcacca*c*c*a-3'

31 mer Toc-2'OMeRNA
                                        (SEQ ID NO: 2)
5'-Toc-u*g*a*auaccaaug*c*uacgcauacgcacca*c*c*a-3'

Second strand
13 mer LNA/DNA gapmer
                                        (SEQ ID NO: 3)
5'-G*C*a*t*t*g*g*t*a*t*T*C*A-3'

13 mer LNA/DNA mixmer
                                        (SEQ ID NO: 4)
5'-G*c*a*t*T*g*g*T*a*t*t*C*A-3'
Capitalized/Underlined: LNA
(C = methylcytosine LNA)
Uncapitalized: DNA
Capitalized: RNA
Uncapitalized/Underlined: 2'-O-Me RNA
*phosphorothioate internucleotide linkage
```

RNA oligonucleotides ranging from 20 to 31 bases were also prepared for use as migration standards in Northern blot analyses:

```
20 mer cRNA
                                        (SEQ ID NO: 5)
5'-GCUACGCAUACGCACCACCA-3'

22 mer cRNA
                                        (SEQ ID NO: 6)
5'-AUGCUACGCAUACGCACCACCA-3'

23 mer cRNA
                                        (SEQ ID NO: 7)
5'-AAUGCUACGCAUACGCACCACCA-3'

24 mer cRNA
                                        (SEQ ID NO: 8)
5'-CAAUGCUACGCAUACGCACCACCA-3'

25 mer cRNA
                                        (SEQ ID NO: 9)
5'-CCAAUGCUACGCAUACGCACCACCA-3'

31 mer cRNA
                                        (SEQ ID NO: 10)
5'-UGAAUACCAAUGCUACGCAUACGCACCACCA-3'
```

(Abbreviations are as above)

A digoxigenin-labeled (DIG) DNA probe for Northern blotting analysis was also prepared:

```
28 mer 3'DIG-DNA
                                        (SEQ ID NO: 11)
5'-tggtgcgtatgcgtagcagtggtattca-DIG-3'
```

(Abbreviations are as above)

The LNA/DNA oligonucleotides were synthesized by Gene Design (Osaka, Japan), and the cRNAs were synthesized by Hokkaido System Science (Sapporo, Japan). The DIG DNA probe was prepared by labeling the DNA oligonucleotide with digoxigenin-ddUTP, using a DIG Oligonucleotide 3'-End Labeling Kit, 2nd Generation (Roche Diagnostics).

The double-stranded agents made up of 31mer Toc-cRNA-G with either 13mer LNA/DNA gapmer (FIG. 7-1A) or 13mer LNA/DNA mixmer (FIG. 7-1B), or 31mer Toc-2'OMeRNA with 13mer LNA/DNA gapmer were prepared by mixing equimolar amounts of each strand in phosphate-buffered saline (Sigma-Aldrich, St. Louis, Mo.), heating the solution to 95 degrees C. for 5 minutes and then cooled to and held at 37 degrees C. for one hour to thereby anneal the nucleic acid strands and form the double-stranded nucleic acid agent. The annealed nucleic acids were stored at 4 degrees C. or on ice. The double-stranded agents were formulated as a PBS solution for in vivo experiments.

In vivo study of the release of the therapeutic oligonucleotide in mice. Female wild type Crlj:CD1 (ICR) mice aged 4-5 weeks (Oriental Yeast, Tokyo, Japan) were kept on a 12-h light/dark cycle in a pathogen-free animal facility with free access to food and water. The double-stranded agents were administered once, to one mouse, respectively, by tail vein injection at 6 mg/kg/dose. A control mouse received injections of PBS. Twenty-four hours after the intravenous injection, the livers were harvested for analysis by Northern blotting. The total RNA in the liver was extracted using ISOGEN II kit (Wako Pure Chemicals, Osaka, Japan).

Northern blotting analysis. Total RNA (30 microg) was separated by electrophoresis on an 18% polyacrylamide-urea gel. The migration standards SEQ ID NO:4-9, as well as the first strand as a single strand were included in separate lanes as controls. The electrophoresed materials were transferred to a Hybond-N+ membrane (Amersham Biosciences, Piscataway, N.J.). The blot was hybridized with the 3'-DIG DNA probe, and visualized with Gene Images instrument. The result comparing the gapmer with the mixmer (FIG. 7-1A vs. 7-1B) is shown in FIG. 7-2D. The result comparing the double-stranded agent having a first strand with a cleavable RNA-based complementary region versus one with a fully 2'-O methylated RNA strand (FIG. 7-1A vs. 7-1C) is shown in FIG. 7-2E. Separate blots were hybridized with the mouse U6 micro RNA sequence as an internal control (not shown).

Results. The blotting analysis in FIG. 7-2D shows that the Toc-cRNA-G first strand in each of the double-stranded agents was cleaved in vivo to a shorter length. Compared to unprocessed Toc-cRNA-G control (Lane M7), the gapmer double-stranded agent (Lane 1) revealed essentially complete conversion of the Toc-cRNA-G first strand to a shorter length. Similarly, the mixmer double-stranded agent (Lane 2) showed significant conversion to shorter length probes. The first strand in both cases was processed to oligonucleotides having from 20 to about 26 bases, based on comparison to migration distances of the control cRNA in Lanes M1-M5.

The blotting analysis in FIG. 7-2E shows that whereas the Toc-cRNA-G strand (with RNA in the RNA-based complementary region)(Lane 1) was cleaved into shorter fragments, the fully 2'-O methylated first strand (Lane 2) was not cleaved, and instead migrated about the same distance as the full length 31mer controls of lanes M6 and M7.

The appearance of the shorter first strand fragments in Lanes 1-2 of FIG. 7-2D and Lane 1 but not Lane 2 of FIG. 7-2E demonstrates that the double-stranded agents were delivered to the liver in vivo, and the double-stranded DNA/RNA heteroduplex complementary region was recognized by RNase H and the first strand was cleaved. The appearance of the some 20mer product in Lanes 1-2 of FIG. 7-2D and Lane 1 of FIG. 7-2E demonstrates that some further processing of the cleaved first strand occurred, probably by an exonuclease to trim the oligonucleotide down to a nuclease-resistant position conferred by the phosphorothioate linkage.

Example 2

An experiment assessing the in vivo inhibition potency of microRNA expression by a double-stranded nucleic acid agent according to an embodiment was conducted. Two conventional single-stranded antisense oligonucleotide controls were compared with the double-stranded agent. The polynucleotide structures are shown in FIG. 8.

The controls were the LNA/DNA mixmer antimir known as miravirsen (registered trademark), and a 2'-O methylated RNA antagomir containing a cholesterol moiety. The latter was annealed with a LNA/DNA gapmer to form the double-stranded agent used in the example. The sequence, composition, and strand length of the strands were as follows:

```
First strand
36 mer RNA strand
                                          (SEQ ID NO: 12)
5'-a*c*aaacaccauugucacacuc*c*a*UGAAUACCAAU*g*c-3'-
chol Second strand
13 mer LNA/DNA gapmer complement
                                          (SEQ ID NO: 13)
5'-G*C*a*t*t*g*g*t*a*t*T*C*A-3'

Single-stranded Control
AntimiR(miR122)
                                          (SEQ ID NO: 14)
5'-C*c*A*t*t*G*T*c*a*C*a*C*t*C*C-3'
```

(Abbreviations are as above)

To prepare the double-stranded agent, the LNA/DNA complement and the 36mer RNA strand were mixed in equimolar amounts, the solution was heated at 95 degrees C. for 5 minutes and then cooled to and held at 37 degrees C. for one hour to thereby anneal the nucleic acid strands and form the double-stranded nucleic acid agent. The annealed nucleic acids were stored at 4 degrees C. or on ice.

In vivo experiment. The mice were 4- to 6-week old female ICR mice with body weights of 20 to 25 g. The experiments using mice were all carried out with n=3. The nucleic agents were intravenously injected to a mouse in an amount of 0.75 mg/kg each through the tail vein. Also, as a negative control group, mice to which only PBS was injected (instead of the nucleic acid agents) were also prepared.

Seventy-two hours after the injection, the mice were perfused with PBS, and then the mice were dissected to extract the liver. Subsequently, mRNA was extracted using the Isogen kit (Gene Design, Inc.) according to the protocol. cDNA was synthesized using SuperScript III (Invitrogen, Inc.) according to the protocol. Quantitative RT-PCR was carried out by TaqMan (Roche Applied Bioscience Corp.). The primers used in the quantitative RT-PCR were products designed and produced by Life Technologies Corp. based on the various gene numbers. The amplification conditions (temperature and time) were: 15 seconds at 95 degrees C., 30 seconds at 60 degrees C., and 1 second at 72 degrees C. (one cycle) was repeated for 40 cycles. Based on the results of the quantitative RT-PCR thus obtained, the amount of expression of microRNA (miR122)/amount of expression of microRNA (SNO234; internal standard gene) were respectively calculated, and the results for each group were compared and evaluated by a t-test. The results are presented in the graph at the bottom of FIG. 8.

Results. As shown by the results in FIG. 8, all three nucleic acid reagents show an inhibition in the expression of miR122 relative to the negative control (PBS only). However, degree of inhibition achieved with the double-stranded agent according to an embodiment is greater than that achieved with single-stranded oligonucleotides, and that difference is statistically significant.

Example 3

An experiment demonstrating the utility of a chimeric double-stranded nucleic acid agent for micro RNA inhibition in vivo was conducted. Specifically, not only the inhibitory effect for microRNA 122 (miR122) which is a direct target of the nucleic acid used in this experiment but also the inhibitory effect for the expression of Aldolase A (ALDOA) and branched chain ketoacid dehydrogenase kinase (BCKDK) mRNA which are downstream targets of miR122 were evaluated. Total serum cholesterol and low-density lipoprotein (LDL) value which are phenotype of ALDOA was also evaluated. A known single-stranded nucleic acid agent which inhibits miR122 was used as a control and the control nucleic acid agent was compared with a heteroduplex nucleic acid into which the known single-stranded nucleic acid was introduced. The nucleic acid structures are shown in FIG. 9. The LNA/DNA mixmer antimiR (miravirsen (registered trademark) was used as a positive control. A group to which PBS was administered was used as a negative control. The sequence, composition, and strand length of the strands were as follows:

```
First strand
28 mer RNA strand
                                           (SEQ ID NO: 15)
5'-C*c*A*t*t*G*T*c*a*C*a*C*t*C*CGCGAUACCAAU*c*g-3'

Second strand
13 mer LNA/DNA gapmer complement
                                           (SEQ ID NO: 16)
5'-C*G*a*t*t*g*g*t*a*t*C*G*C-3'

Single-stranded Control
AntimiR(miR122)
                                           (SEQ ID NO: 14)
5'-C*c*A*t*t*G*T*c*a*C*a*C*t*C*C-3'
```

(Abbreviations are as above)

The double-stranded agent was prepared as Examples 1 and 2. That is, the LNA/DNA complement and the RNA strand were mixed in equimolar amounts, the solution was heated at 95 degrees C. for 5 minutes and then cooled to and held at 37 degrees C. for one hour to thereby anneal the nucleic acid strands and form the double-stranded nucleic acid agent. The annealed nucleic acids were stored at 4 degrees C. or on ice. In vivo experiment The mice were 4-week old female ICR mice with body weights of 20 to 25 g. The experiments using mice were all carried out with n=3. The nucleic acid agents were intravenously injected to a mouse in through the tail vein. The nucleic acid agents were injected to a mouse in an amount of 0.1 mg/kg each once in an experiment for evaluating the inhibitory effect of miR122 (FIG. 10a). Then, the mice were perfused with PBS 72 hours after the injection and hepatic left lobe was collected. The nucleic acid agents were injected to a mouse in an amount of 0.75 mg/kg each three times in a week in an experiment for evaluating ALDOA (FIG. 10b) and BCKDK (FIG. 10c) which are downstream target of miR122 and the total serum cholesterol (FIG. 10c). Then, blood was collected at the injection and 168 hours after it and liver tissue was collected too. RNA extraction, cDNA synthesis and quantitative PCR were conducted by the same protocol with Example 2. The evaluation was carried out by correcting with U6 which is an endogenous control for miRNA which is a direct target (FIG. 10a) and by correcting with GAPDH which is an endogenous control for ALDOA (FIG. 10b) and BCKDK (FIG. 10c). The expression level for each group was compared as Example 2. In the evaluation of phenotype, the reduction from 0 hour after the injection to 168 hours of total serum cholesterol (FIG. 10d) and LDL (low density lipoprotein) (FIG. 10e) were measured and compared with a group to which PBS was injected. For the assessment of dose-dependent effect on phenotype, the nucleic acid agents were injected in an amount of 0.1, 0.75 and 1.5 mg/kg each three times in a week and the reduction of total serum cholesterol were evaluated (FIG. 10f) as same as before.

Results. As shown by the results in FIG. 10a, all three nucleic acid reagents show an inhibition in the expression of miR122 relative to the negative control (PBS only). However, degree of inhibition achieved with the double-stranded agent according to an embodiment is greater than that achieved with single-stranded oligonucleotides, and that difference is statistically significant. As shown by FIGS. 10b and c, double-stranded antimiR showed the statistically-significant elevation of the expression of the downstream targets (ALDOA, BCKDK) of miR122 compared with a single-stranded nucleic acid. As shown by FIGS. 10d and 10e, double-stranded antimiR showed the statistically-significant reduction of total serum cholesterol and LDL compared with a single-stranded nucleic acid. As shown by FIG. 10f, double-stranded antimiR showed the dose-dependent phenotype effect superior to single-stranded antimiR.

Example 4

We conducted an experiment assessing application of a double-stranded nucleic acid agent to other type of oligonucleotide, which has other target and interaction with target RNA. The target RNA was pre-mRNA of dystrophin, which is responsible gene of Duchenne Muscular Dystrophy (DMD). The oligonucleotide in example 4 is splice-switching oligonucleotide (SSO), which induced skipping exon 58 of dystrophin. The polynucleotide structures are shown in FIG. 11.

The controls were single-stranded SSO. The sequence, composition, and strand length of the strands were as follows:

```
First strand
28 mer RNA strand
                                           (SEQ ID NO: 17)
5'-t*C*t*g*G*g*c*T*c*c*T*g*g*T*aGCGAUACCAAU*c*g-3'

Second strand
13 mer LNA/DNA gapmer complement
                                           (SEQ ID NO: 16)
5'-C*G*a*t*t*g*g*t*a*t*C*G*C-3'

Single-stranded Control
15 mer SSO
                                           (SEQ ID NO: 18)
5'-t*C*t*g*G*g*c*T*c*c*T*g*g*T*a-3'
```

(Abbreviations are as above)

The double-stranded agent was prepared as Examples 1 to 3. That is, the LNA/DNA complement and the RNA strand were mixed in equimolar amounts, the solution was heated at 95 degrees C. for 5 minutes and then cooled to and held at 37 degrees C. for one hour to thereby anneal the nucleic acid strands and form the double-stranded nucleic acid agent. The annealed nucleic acids were stored at 4 degrees C. or on ice.

For the experiment, a human dystrophin gene fragment stable expression plasmid was constructed and stable cell lines containing the construct were established. The dystrophin gene fragment has a full-length sequence from Exon 57 to Exon 59 except Intron 57, which was shortened for convenience because of its length. Expression of the dystrophin fragment in the stable cell line would normally be expected to yield an mRNA comprising exons 57, 58, and 59. In the presence of a splice-switching oligonucleotide, which has the ability to cause the skipping of exon 58 during the processing of the pre-mRNA, however, the expressed mRNA would be expected to comprise exon 57 and 59 but to lack exon 58.

In the experiment, to the extent the antisense oligonucleotide (ASO) is able to reach the nucleus, the ASO should be able to alter the splicing of the mRNA product expressed from the dystrophin gene, and thus the amount of the three-exon fragment (exons 57, 58, and 59) of dystrophin would show a corresponding decrease.

Single-stranded antisense oligonucleotides that can cause exon skipping of exon 58 was prepared and tested. The ASO binds to a sequence within exon 58. Construction of Dystrophin Gene Expression Plasmids.

The starting plasmid for construction was the pcDNA5/FRT vector (Invitrogen, Carlsbad, Calif.). To generate fragment containing Flag Tag, two oligonucleotides, 5'-AGCTTACCATGGATTACAAGGACGACGACGACAAGGGGGTAC-3' (SEQ ID NO: 19)(including HindIII and KpnI site, underlined) and 5'-CCCCTTGTCGTCGTCGTCCTTGTAATCCATGGTA-3' (SEQ ID NO: 20) were annealed together. After annealing, the fragment was cloned into HindIII/KpnI sites of pcDNA5/FRT vector (pcDNA5/FRT-FLAG). The Flag Tag contains two silent mutations to avoid the expressions of extra first methionine accidentally.

Using the pcDNA3-EGFP vector as a template, the EGFP fragment was amplified using a forward primer 5'-CCCGGGTGTGAGCAAGGGCGAGGAGCTGT-3' (SEQ ID NO: 21) (including SmaI site, underlined) and a reverse primer 5'-ATAGGGCCC TTACTTGTACAGCTCGTC-CAT-3' (SEQ ID NO: 22) (including ApaI site, underlined). The cycling conditions were: 94 degrees C. for 2 min, then 98 degrees C. for 0.5 min, 63 degrees C. for 0.5 min, 68 degrees C. for 0.75 min for 35 cycles, and 68 degrees C. for 3 min. PCR reactions were carried out using KOD FX NEO (TOYOBO, Osaka, Japan according to the manufacturer's instructions. The EGFP fragment was inserted into SmaI/ApaI digested pcDNA5/FRT-FLAG vector (pcDNA5/FRT-FLAG-EGFP).

Using the pDsRed-Express-N1 vector as a template, the EGFP fragment was amplified using a forward primer 5'-ATATGGATCCAACCGGT GTGGCCTCCTC-GAGGACGTCA-3' (SEQ ID NO: 23) (including BamHI and AgeI site, underlined) and a reverse primer 5'-CGGTC-TACAGGAACAGGTGGTGGC-3' (SEQ ID NO: 24). The cycling conditions were: 94 degrees C. for 2 min, then 98 degrees C. for 0.5 min, 63 degrees C. for 0.5 min, 68 degrees C. for 0.75 min for 35 cycles, and 68 degrees C. for 3 min. PCR reactions were carried out using KOD FX NEO (TOYOBO, Osaka, Japan) according to the manufacturer's instructions. The EGFP fragment was inserted into BamHI/SmaI digested pcDNA5/FRT-FLAG-DsRed vector (pcDNA5/FRT-FLAG-DsRed-EGFP).

To collect fluorescence proteins into nucleus, the NLS sequence (Nucleus Localized Signal) was inserted into BamHI digested pcDNA5/FRT-Flag-DsRed-EGFP. The NLS sequence was prepared by annealing two oligonucleotides 5'-ATGCCC-CAAAAAAAAAACGCAAAGTG-GAGGACCCAAAGGTACCAAAG-3' (SEQ ID NO: 25) and 5'-GATCCTTTGGTACCTTTGGGTCCTC-CACTTTGCGTTTTTTTTTGGGGCATGTAC-3' (SEQ ID NO: 26) (pcDNA5/FRT-Flag-NLS-DsRed-EGFP).

To generate human Dystrophin gene stable expression plasmids, a human Dystrophin gene fragment was obtained by means of PCR with a HepG2 genome. The plasmid which contains Dystrophin gene fragment has a full-length sequence from Exon 57 to Exon 59 except Intron 57. Intron 57 sequence (17683 base pairs) is too long for inserting into plasmid, therefore a portion of Intron 57, sequence +207 to +17486, was deleted by means of PCR using a forward primer 5'-AACGGTACC AACGCTGCT-GTTCTTTTTCA-3' (SEQ ID NO: 27) (including KpnI site, underlined), a reverse primer 5'-AAATCGTCCATTA-CAAACACAGCGCTTTCC-3' (SEQ ID NO: 28) and forward primer 5'-GTGTTTGTAATGGACGATTTCT-TAAAGGGTATT-3' (SEQ ID NO: 29), reverse primer 5'-AGACCGGTACTCCTCAGCCTGCTTTCGTA-3' (SEQ ID NO: 30) (including AgeI site, underlined). The fragment was cloned into KpnI/AgeI digested pcDNA5/FRT-Flag-NLS-DsRed-EGFP vector (pcDNA5/FRT-Flag-NLS-DMD-Exon57_58_59(short-Intron57)-DsRed-EGFP).

All constructs were verified by ABI PRISM 310 Analyzer (Applied Biosystems, Foster City, Calif., USA) or sequencing by Fasmac (Kanagawa, Japan).

Stable Cell Line Establishment. Flp-In-293 (Invitrogen, Carlsbad, Calif.) cells were cultured in Dulbecco's Modified Eagle's Medium (DMEM) (Nacalaitesque, Kyoto, Japan) supplemented with 10% fetal bovine serum containing 10% fetal bovine serum (FBS) (Biowest, Nuaille, France), 2% Penicillin-Streptomycin Mixed Solution (Penicillin 10,000 units/mL, Streptomycin 10,000 microg/mL) (Nacalaitesque, Kyoto, Japan) and selected with 100 mg/mL Zeocin at 37 degrees C. The pcDNA5/FRT-Flag-Dys57>59di-NLS-DsRed-EGFP and pOG44 (the Flp recombinase expression plasmid) (Invitrogen, Carlsbad, Calif.) were co-transfected into the Flp-In-293 cells. Stable cell lines were selected on the basis of Hygromycin B 50 mg/mL (Invitrogen, Carlsbad, Calif.) resistance.

Cell Culture. The stable cell line was cultured in Dulbecco's Modified Eagle's Medium (DMEM) (Nacalaitesque, Kyoto, Japan) containing 10% fetal bovine serum (FBS) (Biowest, Nuaille, France) and 2% Penicillin-Streptomycin Mixed Solution (Penicillin 10,000 u/mL, Streptomycin 10,000 microg/mL) (Nacalaitesque, Kyoto, Japan).

In vitro experiment. The cells were plated in serum-containing medium without antibiotics in 24-well plates. For lipid-based transfections, either the single-stranded control and double stranded agents were mixed with Lipofectamine RNAiMAX (Invitrogen) following the manufacturer's instructions and incubated with cells in serum-free media for 4 hours. Cells were washed once with PBS and incubated for 20 hours in full media containing antibiotics, before RNA extraction. mRNA was extracted using the Isogen kit (Gene Design, Inc.) following the manufacturer's instructions. cDNA was synthesized using Transcriptor Universal cDNA Master (Roche Applied Bioscience Corp.) according to the protocol. Quantitative RT-PCR was carried out by SYBR Green Real Time PCR Master Mix (Roche Applied Bioscience Corp). The sequences of primers are shown below.

```
Exon 58 Skip analysis primers:
                                        SEQ ID NO: 31
5'-AACGGTACCAACGCTGCTGTTCTTTTTCA-3'

SEQ ID NO: 32
5'-CTTGGAGCCGTACTGGAACT-3'

GAPDH analysis primers:
                                        SEQ ID NO: 33
5'-ACCACAGTCCATGCCATCAC-3'

SEQ ID NO: 34
5'-TCCACCACCCTGTTGCTGTA-3'
```

All primers were synthesized by Hokkaido System Sciences (Sapporo, Japan). The amplification conditions (temperature and time) were: 10 seconds at 98 degrees C., 15 seconds at 55 degrees C., and 15 second at 72 degrees C. (one cycle) was repeated for 35 cycles. Based on the results of the quantitative RT-PCR thus obtained, the amount of expression of exon-skipped dystrophin/amount of expression of glyceraldehyde 3-phosphate dehydrogenase (GAPDH; internal standard gene) were respectively calculated, and the results for each group were compared to control group and evaluated by a t-test. The results are presented in the graph of FIG. 12.

Results. As shown by the results in FIG. 12, degree of exon-skipping achieved with the double-stranded agent according to an embodiment is greater than that achieved with single-stranded oligonucleotides, and that difference is statistically significant.

Example 5

We conducted an experiment assessing application of a double-stranded nucleic acid agent to other type of antisense oligonucleotide, which has other target and chemical structure. The target was intron of pre-mRNA, apolipoprotein B. The polynucleotide structures are shown in FIG. 13.

The controls were the LNA/DNA gapmer. The sequence, composition, and strand length of the strands were as follows:

```
First strand
29 mer RNA strand
                                        (SEQ ID NO: 35)
5'-C*T*C*c*c*a*c*c*a*c*a*t*a*G*C*AGCGAUACCAAU*c*
g-3'

Second strand
13 mer LNA/DNA gapmer complement
                                        (SEQ ID NO: 16)
5'-C*G*a*t*t*g*g*t*a*t*C*G*C-3'

Single-stranded Control
16 mer intron gapmer
                                        (SEQ ID NO: 36)
5'-C*T*C*c*c*a*c*c*a*c*a*t*a*G*C*A-3'
```

(Abbreviations are as above)

The double-stranded agent was prepared as Examples 1 to 3. That is, the LNA/DNA complement and the RNA strand were mixed in equimolar amounts, the solution was heated at 95 degrees C. for 5 minutes and then cooled to and held at 37 degrees C. for one hour to thereby anneal the nucleic acid strands and form the double-stranded nucleic acid agent. The annealed nucleic acids were stored at 4 degrees C. or on ice.

In vitro experiment. Huh-7 (human hepato cellular carcinoma cell line-7) cells were cultured under recommended media conditions. The cells were plated in serum-containing medium without antibiotics in 24-well plates. For lipid-based transfections, either the single-stranded control and double stranded agents were mixed with Lipofectamine RNAiMAX (Invitrogen) following the manufacturer's instructions and incubated with cells in serum-free media for 4 hours. Cells were washed once with PBS and incubated for 20 hours in full media containing antibiotics, before RNA extraction. mRNA was extracted using the Isogen kit (Gene Design, Inc.) following the manufacturer's instructions. cDNA was synthesized using Transcriptor Universal cDNA Master (Roche Applied Bioscience Corp.) according to the protocol. Quantitative RT-PCR was carried out by TaqMan (Roche Applied Bioscience Corp.). The primers used in the quantitative RT-PCR were products designed and produced by Life Technologies Corp. based on the various gene numbers. The amplification conditions (temperature and time) were: 15 seconds at 95 degrees C., 30 seconds at 60 degrees C., and 1 second at 72 degrees C. (one cycle) was repeated for 40 cycles. Based on the results of the quantitative RT-PCR thus obtained, the amount of expression of ApoB/amount of expression of glyceraldehyde 3-phosphate dehydrogenase (GAPDH; internal standard gene) were respectively calculated, and the results for each group were compared and evaluated by a t-test. The results are presented in the graph of FIG. 14.

Results. As shown by the results in FIG. 14, the single-stranded intron gapmer didn't show an inhibition in the expression of ApoB mRNA relative to the negative control (Lipofectamine only). However, the double-stranded agent according to an embodiment achieved the significant inhibition of ApoB mRNA.

Example 6

We conducted an experiment assessing application of a double-stranded nucleic acid agent, which second strand was changed from 13mer LNA/DNA Gapmer to 13mer LNA/DNA Mixmer. The target was same as Example 2-3, micro RNA 122. The polynucleotide structures are shown in FIG. 15.

The controls were a 2'-O methylated RNA antagomir. The sequence, composition, and strand length of the strands were as follows:

```
First strand
36 mer RNA strand
                                        (SEQ ID NO: 37)
5'-a*c*aaacaccauugucacacuc*c*a*UGAAUACCAAU*g*c-3'

Second strand
13 mer LNA/DNA mixmer complement
                                        (SEQ ID NO: 4)
5'-G*c*a*t*T*g*g*T*a*t*t*C*A-3'

Single-stranded Control
23 mer antagomiR(miR122)
                                        (SEQ ID NO: 38)
5'-a*c*aaacaccauugucacacuc*c*a-3'
```

(Abbreviations are as above)

The double-stranded agent was prepared as Examples 1 to 5. That is, the LNA/DNA complement and the RNA strand were mixed in equimolar amounts, the solution was heated at 95 degrees C. for 5 minutes and then cooled to and held at 37 degrees C. for one hour to thereby anneal the nucleic acid strands and form the double-stranded nucleic acid agent. The annealed nucleic acids were stored at 4 degrees C. or on ice.

In vitro experiment. Huh-7 (human hepato cellular carcinoma cell line-7) cells were cultured under recommended media conditions. The cells were plated in serum-containing medium without antibiotics in 24-well plates. For lipid-based transfections, either the single-stranded control and double stranded agents were mixed with Lipofectamine 2000 (Invitrogen) following the manufacturer's instructions and incubated with cells in serum-free media for 4 hours. Cells were washed once with PBS and incubated for 20 hours in full media containing antibiotics, before RNA extraction. mRNA was extracted using the Isogen kit (Gene Design, Inc.) following the manufacturer's instructions. cDNA was synthesized using Transcriptor Universal cDNA Master (Roche Applied Bioscience Corp.) according to the protocol. Quantitative RT-PCR was carried out by TaqMan (Roche Applied Bioscience Corp.). The primers used in the quantitative RT-PCR were products designed and produced by Life Technologies Corp. based on the various gene numbers. The amplification conditions (temperature and time) were: 15 seconds at 95 degrees C., 30 seconds at 60 degrees C., and 1 second at 72 degrees C. (one cycle) was repeated for 40 cycles. Based on the results of the quantitative RT-PCR thus obtained, the amount of expression of microRNA (miR122)/amount of expression of microRNA (U6; internal standard gene) were respectively calculated, and the results for each group were compared and evaluated by a t-test. The results are presented in the graph of FIG. 16.

Results. both nucleic acid reagents show an inhibition in the expression of miR122 relative to the negative control (Lipofectamine only). However, degree of inhibition achieved with the double-stranded agent according to an embodiment is greater than that achieved with single-stranded oligonucleotides, and that difference is statistically significant.

Example 7

We conducted an experiment assessing application of another double-stranded nucleic acid agent, which second strand was changed from 13mer LNA/DNA Gapmer to 13mer LNA/DNA Mixmer. The target was same as Example 4, pre-mRNA of dystrophin. The oligonucleotide in example 6 is splice-switching oligonucleotide (SSO), which induced skipping exon 58 of dystrophin. The polynucleotide structures are shown in FIG. 17.

The controls were single-stranded SSO. The sequence, composition, and strand length of the strands were as follows:

```
First strand
28 mer RNA strand
                                       (SEQ ID NO: 17)
5'-t*C*t*g*G*g*c*T*c*c*T*g*g*T*aGCGAUACCAAU*c*g-3'

Second strand
13 mer LNA/DNA mixmer complement
                                       (SEQ ID NO: 4)
5'-G*c*a*t*T*g*g*T*a*t*t*C*A-3'

Single-stranded Control
15 mer SSO
                                       (SEQ ID NO: 18)
5'-t*C*t*g*G*g*c*T*c*c*T*g*g*T*a-3'
```

(Abbreviations are as above)

The double-stranded agent was prepared as Examples 1 to 6. That is, the LNA/DNA complement and the RNA strand were mixed in equimolar amounts, the solution was heated at 95 degrees C. for 5 minutes and then cooled to and held at 37 degrees C. for one hour to thereby anneal the nucleic acid strands and form the double-stranded nucleic acid agent. The annealed nucleic acids were stored at 4 degrees C. or on ice.

In vitro experiment. The experimental conditions were the same with Example 4.

Results. As shown by the results in FIG. 18, degree of exon-skipping achieved with the double-stranded agent according to an embodiment is greater than that achieved with single-stranded oligonucleotides, and that difference is statistically significant.

Example 8

We conducted an experiment assessing application of another double-stranded nucleic acid agent, which second strand was changed from 13mer LNA/DNA Gapmer to 13mer LNA/DNA Mixmer. The target was same as Example 5, intron of pre-mRNA, apolipoprotein B. The polynucleotide structures are shown in FIG. 19.

The controls were the LNA/DNA gapmer. The sequence, composition, and strand length of the strands were as follows:

```
First strand
29 mer RNA strand
                                       (SEQ ID NO: 35)
5'-C*T*C*c*c*a*c*c*a*c*a*t*a*G*C*AGCGAUACCAAU*c* g-3'

Second strand
13 mer LNA/DNA mixmer complement
                                       (SEQ ID NO: 4)
5'-G*c*a*t*T*g*g*T*a*t*t*C*A-3'

Single-stranded Control
16 mer intron gapmer
                                       (SEQ ID NO: 36)
5'-C*T*C*c*c*a*c*c*a*c*a*t*a*G*C*A-3'
```

(Abbreviations are as above)

The double-stranded agent was prepared as Examples 1 to 3. That is, the LNA/DNA complement and the RNA strand were mixed in equimolar amounts, the solution was heated at 95 degrees C. for 5 minutes and then cooled to and held at 37 degrees C. for one hour to thereby anneal the nucleic acid strands and form the double-stranded nucleic acid agent. The annealed nucleic acids were stored at 4 degrees C. or on ice.

In vitro experiment. The experimental conditions were the same with Example 5.

Results. As shown by the results in FIG. 20, the single-stranded intron gapmer didn't show an inhibition in the expression of ApoB mRNA relative to the negative control (Lipofectamine only). However, the double-stranded agent according to an embodiment achieved the significant inhibition of ApoB mRNA in a dose-dependent manner.

Example 9

We conducted an experiment assessing application of a double-stranded nucleic acid agent, which place of nucleic acid agent was changed from 5'-end of RNA strand to 3'-end. The target was same as Example 2-3, micro RNA 122. The polynucleotide structures are shown in FIG. 21.

The controls was the LNA/DNA mixmer antimiR122 (miravirsen (registered trademark)). The sequence, composition, and strand length of the strands were as follows:

```
First strand
28 mer RNA strand-5'
                                           (SEQ ID NO: 15)
5'-C*c*A*t*t*G*T*c*a*C*a*C*t*C*CGCGAUACCAAU*c*g-3'

28 mer RNA strand-3'
                                           (SEQ ID NO: 39)
5'-g*c*g*AUACCAAUCGC*c*A*t*t*G*T*c*a*C*a*C*t*C*

C-3'

Second strand
13 mer LNA/DNA mixmer complement
                                           (SEQ ID NO: 16)
5'-C*G*a*t*t*g*g*t*a*t*C*G*C-3'

Single-stranded Control
23 mer AntimiR(miR122)
                                           (SEQ ID NO: 14)
5'-C*c*A*t*t*G*T*c*a*C*a*C*t*C*C-3'
```

(Abbreviations are as above)

The double-stranded agent was prepared as Examples 1 to 5. That is, the LNA/DNA complement and the RNA strand were mixed in equimolar amounts, the solution was heated at 95 degrees C. for 5 minutes and then cooled to and held at 37 degrees C. for one hour to thereby anneal the nucleic acid strands and form the double-stranded nucleic acid agent. The annealed nucleic acids were stored at 4 degrees C. or on ice.

In vitro experiment.

Huh-7 (human hepato cellular carcinoma cell line-7) cells were cultured under recommended media conditions. The cells were plated in serum-containing medium without antibiotics in 24-well plates. For lipid-based transfections, either the single-stranded control and double stranded agents were mixed with Lipofectamine RNAi MAX (Invitrogen) following the manufacturer's instructions and incubated with cells in serum-free media for 4 hours. Cells were washed once with PBS and incubated for 20 hours in full media containing antibiotics, before RNA extraction. Micro RNA was extracted using the Isogen kit (Gene Design, Inc.) following the manufacturer's instructions. cDNA was synthesized using Transcriptor Universal cDNA Master (Roche Applied Bioscience Corp.) according to the protocol. Quantitative RT-PCR was carried out by TaqMan (Roche Applied Bioscience Corp.). The primers used in the quantitative RT-PCR were products designed and produced by Life Technologies Corp. based on the various gene numbers. The amplification conditions (temperature and time) were: 15 seconds at 95 degrees C., 30 seconds at 60 degrees C., and 1 second at 72 degrees C. (one cycle) was repeated for 40 cycles. Based on the results of the quantitative RT-PCR thus obtained, the amount of expression of microRNA (miR122)/amount of expression of microRNA (U6; internal standard gene) were respectively calculated, and the results for each group were compared and evaluated by a t-test. The results are presented in the graph in FIG. 22.

Results. Both double-stranded antimiR-5' and antimiR-3' show an inhibition in the expression of miR122 relative to the negative control (Lipofectamine only) and single-stranded antimiR. However, degree of inhibition achieved with the double-stranded antimiR-3' is less than that achieved with double-stranded antimiR-5'.

Result

As shown by the result in FIG. 22, all three nucleic acid reagents show an inhibition in the expression of miR122 relative to the negative control (PBS only). However, degree of inhibition achieved with the double-stranded antimiR-5' is more than that achieved with double-stranded antimiR-3', and that difference is statistically significant.

SEQUENCE LISTING FREE TEXT 1-20, 35-39 Synthetic
21-34 Primer

The invention claimed is:

1. A double-stranded nucleic acid agent comprising a first nucleic acid strand annealed to a second nucleic acid strand, wherein:
the first nucleic acid strand comprises
(i) an RNA region with 8-11 consecutive natural RNA nucleotides that can be recognized by RNase H when the first nucleic acid strand is hybridized to the second nucleic acid strand,
(ii) a therapeutic oligonucleotide region wherein at least one internucleotide linkage at the 3' end and at the 5' end of the therapeutic oligonucleotide region is more nuclease-resistant than a natural internucleotide linkage, wherein the at least one nuclease-resistant internucleotide linkage is a phosphorothioate group, and wherein the therapeutic oligonucleotide region is
(a) a single-stranded region that hybridizes to a precursor mRNA (pre-mRNA) or a micro-RNA, but does not hybridize to the second nucleic acid strand,
(b) a splice-switching oligonucleotide, an intron targeting gapmer, or an antagomir,
(c) linked to the 3' end or 5' end of the RNA region of the first nucleic acid strand, and
(d) released from the double-stranded nucleic acid agent in vivo via RNase H-mediated cleavage of the RNA region of (c), and
(e) comprised of one or more of modified nucleotides, nucleotide analogues, or DNA nucleotides comprising a phosphorothioate group, and
(iii) at least one internucleotide linkage at the 3' end and at the 5' end of the RNA region of the first nucleic acid strand is more nuclease-resistant than a natural internucleotide linkage, wherein the at least one nuclease-resistant internucleotide linkage is a phosphorothioate group, and
the second nucleic acid strand comprises
(i) a 13 consecutive DNA/LNA gapmer or DNA/LNA mixmer region that is hybridized to the RNA region of the first nucleic acid strand and can promote the recognition of the 8-11 consecutive natural RNA nucleotides in the first nucleic acid strand by RNase H, and
(ii) at least one internucleotide linkage at the 3' end and at the 5' end of the second nucleic acid strand is more nuclease-resistant than a natural internucleotide linkage, wherein the at least one nuclease-resistant internucleotide linkage is a phosphorothioate group,
and wherein
the double-stranded nucleic acid agent further comprises a targeting moiety which is (a) selected from a lipid, a sugar, a peptide, and a protein and (b) joined to the 3'-terminal nucleotide or the 5'-terminal nucleotide of the second nucleic acid strand, or to the 3'-terminal nucleotide or the 5'-terminal nucleotide of the first nucleic acid strand.

2. The double-stranded nucleic acid agent according to claim 1, wherein the first nucleic acid strand comprises one or more nucleotides selected from modified RNA nucleotides and nucleotide analogs located 5' and located 3' to the 8-11 consecutive natural RNA nucleotides that can be recognized by RNase H.

3. The double-stranded nucleic acid agent according to claim 2, wherein the one or more nucleotides located 5' and located 3' to the 8-11 consecutive natural RNA nucleotides that can be recognized by RNase H are independently selected from LNA nucleotides, BNA nucleotides, 2'-O-Me RNA nucleotides, and 2'-O-methoxyethyl RNA nucleotides.

4. A method of delivering a therapeutic oligonucleotide to a cell comprising:
contacting with the cell a composition comprising the double-stranded nucleic acid agent according to claim 1.

5. A double-stranded nucleic acid agent comprising a first nucleic acid strand annealed to a second nucleic acid strand, wherein:
the first nucleic acid strand comprises
(i) an RNA region with 8-11 consecutive natural RNA nucleotides that can be recognized by RNase H when the first nucleic acid strand is hybridized to the second nucleic acid strand,
(ii) the therapeutic oligonucleotide region wherein at least one internucleotide linkage at the 3' end and at the 5' end of the therapeutic oligonucleotide region is more nuclease-resistant than a natural internucleotide linkage, wherein the at least one nuclease-resistant internucleotide linkage is a phosphorothioate group, and wherein the therapeutic oligonucleotide region is
(a) a single-stranded region that hybridizes to a precursor mRNA (pre-mRNA) or a micro-RNA, but does not hybridize to the second nucleic acid strand,
(b) a splice-switching oligonucleotide, an intron targeting gapmer, or an antagomir,
(c) linked to the 3' end or 5' end of the RNA region of the first nucleic acid strand, and
(d) released from the double-stranded nucleic acid agent in vivo via RNase H-mediated cleavage of the RNA region of (c), and
(e) comprised of one or more of modified nucleotides, nucleotide analogues, or DNA nucleotides comprising a phosphorothioate group, and (iii) at least one internucleotide linkage at the 3' end and at the 5' end of the RNA region of the first nucleic acid strand is more nuclease-resistant than a natural internucleotide linkage, wherein the at least one nuclease-resistant internucleotide linkage is a phosphorothioate group, and the second nucleic acid strand comprises (i) a plurality of regions consisting of 2 or 3 consecutive DNA nucleotides that hybridize to the RNA region of the first nucleic acid strand and promote the recognition of the 8-11 consecutive natural RNA nucleotides in the first nucleic acid strand by RNase H in a mammalian cell, and (ii) at least one internucleotide linkage at the 3' end and at the 5' end of the second nucleic acid strand is more nuclease-resistant than a natural internucleotide linkage, wherein the at least one nuclease-resistant internucleotide linkage is a phosphorothioate group.

6. The double-stranded nucleic acid agent according to claim 5, wherein the antagomir oligonucleotide is a mixmer, is composed of one type of nucleotide or nucleotide analogue, or is a gapmer.

7. The double-stranded nucleic acid agent according to claim 6, wherein the antagomir oligonucleotide comprises at least one nucleotide selected from 2'-OMe RNA, MOE, CET, ENA, LNA and AmNA, and at least one internucleotide linkage is optionally phosphorothioated.

* * * * *

SEQUENCE LISTING

```
<160> NUMBER OF SEQ ID NOS: 39

<210> SEQ ID NO 1
<211> LENGTH: 31
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (12)..(13), (13)..(14),
      (28)..(29), (29)..(30), (30)..(31)
<223> OTHER INFORMATION: Phosphorothioate linkage
<220> FEATURE:
<221> NAME/KEY: misc_feature
<222> LOCATION: (1)..(1), (2)..(2), (3)..(3), (12)..(12), (13)..(13),
      (14)..(14), (15)..(15), (16)..(16), (17)..(17), (18)..(18),
      (19)..(19), (20)..(20), (21)..(21), (22)..(22), (23)..(23),
      (24)..(24), (25)..(25), (26)..(26), (27)..(27), (28)..(28),
      (29)..(29), (30)..(30), (31)..(31)
<223> OTHER INFORMATION: 2-o-Me

<400> SEQUENCE: 1
ugaauaccaa ugcuacgcau acgcaccacc a                           31

<210> SEQ ID NO 2
<211> LENGTH: 31
```

```
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (12)..(13), (13)..(14),
      (28)..(29), (29)..(30), (30)..(31)
<223> OTHER INFORMATION: Phosphorothioate linkage
<220> FEATURE:
<221> NAME/KEY: misc_feature
<222> LOCATION: (1)..(1), (2)..(2), (3)..(3), (4)..(4), (5)..(5),
      (6)..(6), (7)..(7), (8)..(8), (9)..(9), (10)..(10), (11)..(11),
      (12)..(12), (13)..(13), (14)..(14), (15)..(15), (16)..(16),
      (17)..(17), (18)..(18), (19)..(19), (20)..(20), (21)..(21),
      (22)..(22), (23)..(23), (24)..(24), (25)..(25), (26)..(26),
      (27)..(27), (28)..(28), (29)..(29), (30)..(30), (31)..(31)
<223> OTHER INFORMATION: 2-o-Me

<400> SEQUENCE: 2
ugaauaccaa ugcuacgcau acgcaccacc a                              31

<210> SEQ ID NO 3
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6),
      (6)..(7), (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (1)..(1), (2)..(2), (11)..(11), (12)..(12), (13)..(13)
<223> OTHER INFORMATION: LNA

<400> SEQUENCE: 3
gcattggtat tca                                                  13

<210> SEQ ID NO 4
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6),
      (6)..(7), (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (1)..(1), (5)..(5), (8)..(8), (12)..(12), (13)..(13)
<223> OTHER INFORMATION: LNA

<400> SEQUENCE: 4
gcattggtat tca                                                  13

<210> SEQ ID NO 5
<211> LENGTH: 20
<212> TYPE: RNA
<213> ORGANISM: Artificial
<220> FEATURE:
<223> OTHER INFORMATION: Synthetic

<400> SEQUENCE: 5
gcuacgcaua cgcaccacca                                           20
```

```
<210> SEQ ID NO 6
<211> LENGTH: 22
<212> TYPE: RNA
<213> ORGANISM: Artificial
<220> FEATURE:
<223> OTHER INFORMATION: Synthetic

<400> SEQUENCE: 6
augcuacgca uacgcaccac ca                                            22

<210> SEQ ID NO 7
<211> LENGTH: 23
<212> TYPE: RNA
<213> ORGANISM: Artificial
<220> FEATURE:
<223> OTHER INFORMATION: Synthetic

<400> SEQUENCE: 7
aaugcuacgc auacgcacca cca                                           23

<210> SEQ ID NO 8
<211> LENGTH: 24
<212> TYPE: RNA
<213> ORGANISM: Artificial
<220> FEATURE:
<223> OTHER INFORMATION: Synthetic

<400> SEQUENCE: 8
caaugcuacg cauacgcacc acca                                          24

<210> SEQ ID NO 9
<211> LENGTH: 25
<212> TYPE: RNA
<213> ORGANISM: Artificial
<220> FEATURE:
<223> OTHER INFORMATION: Synthetic

<400> SEQUENCE: 9
ccaaugcuac gcauacgcac cacca                                         25

<210> SEQ ID NO 10
<211> LENGTH: 31
<212> TYPE: RNA
<213> ORGANISM: Artificial
<220> FEATURE:
<223> OTHER INFORMATION: Synthetic

<400> SEQUENCE: 10
ugaauaccaa ugcuacgcau acgcaccacc a                                  31

<210> SEQ ID NO 11
<211> LENGTH: 28
<212> TYPE: DNA
<213> ORGANISM: Artificial
<220> FEATURE:
<223> OTHER INFORMATION: Synthetic

<400> SEQUENCE: 11
tggtgcgtat gcgtagcagt ggtattca                                      28

<210> SEQ ID NO 12
<211> LENGTH: 36
<212> TYPE: RNA
<213> ORGANISM: Artificial
<220> FEATURE:
<223> OTHER INFORMATION: Synthetic
```

```
<220> FEATURE:
<221> NAME/KEY: misc_feature
<222> LOCATION: (1)..(2), (2)..(3), (21)..(22), (22)..(23), (23)..(24),
      (34)..(35), (35)..(36)
<223> OTHER INFORMATION: Phosphorothioate linkage
<220> FEATURE:
<221> NAME/KEY: misc_feature
<222> LOCATION: (1)..(1), (2)..(2), (3)..(3), (4)..(4), (5)..(5),
      (6)..(6), (7)..(7), (8)..(8), (9)..(9), (10)..(10), (11)..(11),
      (12)..(12), (13)..(13), (14)..(14), (15)..(15), (16)..(16),
      (17)..(17), (18)..(18), (19)..(19), (20)..(20), (21)..(21),
      (22)..(22), (23)..(23), (35)..(35), (36)..(36)
<223> OTHER INFORMATION: 2-o-Me

<400> SEQUENCE: 12
acaaacacca uugucacacu ccaugaauac caaugc                                36

<210> SEQ ID NO 13
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6),
      (6)..(7), (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (1)..(1), (2)..(2), (11)..(11), (12)..(12), (13)..(13)
<223> OTHER INFORMATION: LNA

<400> SEQUENCE: 13
gcattggtat tca                                                        13

<210> SEQ ID NO 14
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6),
      (6)..(7), (7)..(8), (8)..(9), (9)..(10), (10)..(11), (11)..(12),
      (12)..(13), (13)..(14), (14)..(15)
<223> OTHER INFORMATION: Phosphorothioate linkage
<220> FEATURE:
<221> NAME/KEY: misc_feature
<222> LOCATION: (1)..(1), (3)..(3), (6)..(6), (7)..(7), (10)..(10),
      (12)..(12), (14)..(14), (15)..(15)
<223> OTHER INFORMATION: LNA

<400> SEQUENCE: 14
ccattgtcac actcc                                                      15

<210> SEQ ID NO 15
<211> LENGTH: 28
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (1)..(2), (2)..(3), (3)..(4), (4)..(5), (5)..(6),
      (6)..(7), (7)..(8), (8)..(9), (9)..(10), (10)..(11), (11)..(12),
      (12)..(13), (13)..(14), (14)..(15), (26)..(27), (27)..(28)
<223> OTHER INFORMATION: Phosphorothioate linkage
<220> FEATURE:
```

<221> NAME/KEY: misc_feature
<222> LOCATION: (1)..(1), (3)..(3), (6)..(6), (7)..(7), (10)..(10),
      (12)..(12), (14)..(14), (15)..(15)
<223> OTHER INFORMATION: LNA
<220> FEATURE:
<221> NAME/KEY: misc_feature
<222> LOCATION: (27)..(27), (28)..(28)
<223> OTHER INFORMATION: 2-o-Me

<400> SEQUENCE: 15
ccattgtcac actccgcgau accaaucg                                             28

<210> SEQ ID NO 16
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6),
      (6)..(7), (7)..(8), (8)..(9), (9)..(10), (10)..(11), (11)..(12),
      (12)..(13)
<223> OTHER INFORMATION: Phosphorothioate linkage
<220> FEATURE:
<221> NAME/KEY: misc_feature
<222> LOCATION: (1)..(1), (2)..(2), (11)..(11), (12)..(12), (13)..(13)
<223> OTHER INFORMATION: LNA

<400> SEQUENCE: 16
cgattggtat cgc                                                             13

<210> SEQ ID NO 17
<211> LENGTH: 28
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (1)..(2), (2)..(3), (3)..(4), (4)..(5), (5)..(6),
      (6)..(7), (7)..(8), (8)..(9), (9)..(10), (10)..(11), (11)..(12),
      (12)..(13), (13)..(14), (14)..(15), (26)..(27), (27)..(28)
<223> OTHER INFORMATION: Phosphorothioate linkage
<220> FEATURE:
<221> NAME/KEY: misc_feature
<222> LOCATION: (2)..(2), (5)..(5), (8)..(8), (11)..(11), (14)..(14)
<223> OTHER INFORMATION: LNA
<220> FEATURE:
<221> NAME/KEY: misc_feature
<222> LOCATION: (27)..(27), (28)..(28)
<223> OTHER INFORMATION: 2-o-Me

<400> SEQUENCE: 17
tctgggctcc tggtagcgau accaaucg                                             28

<210> SEQ ID NO 18
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (3)..(4), (4)..(5), (5)..(6),
      (6)..(7), (7)..(8), (8)..(9), (9)..(10), (10)..(11), (11)..(12),
      (12)..(13), (13)..(14), (14)..(15)
<223> OTHER INFORMATION: Phosphorothioate linkage
<220> FEATURE:
<221> NAME/KEY: misc_feature
<222> LOCATION: (2)..(2), (5)..(5), (8)..(8), (11)..(11), (14)..(14)

<223> OTHER INFORMATION: LNA

<400> SEQUENCE: 18
tctgggctcc tggta                                                          15

<210> SEQ ID NO 19
<211> LENGTH: 42
<212> TYPE: DNA
<213> ORGANISM: Artificial
<220> FEATURE:
<223> OTHER INFORMATION: Synthetic

<400> SEQUENCE: 19
agcttaccat ggattacaag gacgacgacg acaagggggt ac                            42

<210> SEQ ID NO 20
<211> LENGTH: 34
<212> TYPE: DNA
<213> ORGANISM: Artificial
<220> FEATURE:
<223> OTHER INFORMATION: Synthetic

<400> SEQUENCE: 20
ccccttgtcg tcgtcgtcct tgtaatccat ggta                                     34

<210> SEQ ID NO 21
<211> LENGTH: 29
<212> TYPE: DNA
<213> ORGANISM: Artificial
<220> FEATURE:
<223> OTHER INFORMATION: Primer

<400> SEQUENCE: 21
cccgggtgtg agcaagggcg aggagctgt                                           29

<210> SEQ ID NO 22
<211> LENGTH: 30
<212> TYPE: DNA
<213> ORGANISM: Artificial
<220> FEATURE:
<223> OTHER INFORMATION: Primer

<400> SEQUENCE: 22
atagggccct tacttgtaca gctcgtccat                                          30

<210> SEQ ID NO 23
<211> LENGTH: 39
<212> TYPE: DNA
<213> ORGANISM: Artificial
<220> FEATURE:
<223> OTHER INFORMATION: Primer

<400> SEQUENCE: 23
atatggatcc aaccggtgtg gcctcctccg aggacgtca                                39

<210> SEQ ID NO 24
<211> LENGTH: 24
<212> TYPE: DNA
<213> ORGANISM: Artificial
<220> FEATURE:
<223> OTHER INFORMATION: Primer

<400> SEQUENCE: 24
cggtctacag gaacaggtgg tggc                                                24

```
<210> SEQ ID NO 25
<211> LENGTH: 47
<212> TYPE: DNA
<213> ORGANISM: Artificial
<220> FEATURE:
<223> OTHER INFORMATION: Primer

<400> SEQUENCE: 25
atgccccaaa aaaaaaacgc aaagtggagg acccaaaggt accaaag            47

<210> SEQ ID NO 26
<211> LENGTH: 55
<212> TYPE: DNA
<213> ORGANISM: Artificial
<220> FEATURE:
<223> OTHER INFORMATION: Primer

<400> SEQUENCE: 26
gatcctttgg tacctttggg tcctccactt tgcgtttttt ttttggggca tgtac   55

<210> SEQ ID NO 27
<211> LENGTH: 29
<212> TYPE: DNA
<213> ORGANISM: Artificial
<220> FEATURE:
<223> OTHER INFORMATION: Primer

<400> SEQUENCE: 27
aacggtacca acgctgctgt tcttttttca                                29

<210> SEQ ID NO 28
<211> LENGTH: 30
<212> TYPE: DNA
<213> ORGANISM: Artificial
<220> FEATURE:
<223> OTHER INFORMATION: Primer

<400> SEQUENCE: 28
aaatcgtcca ttacaaacac agcgctttcc                                30

<210> SEQ ID NO 29
<211> LENGTH: 33
<212> TYPE: DNA
<213> ORGANISM: Artificial
<220> FEATURE:
<223> OTHER INFORMATION: Primer

<400> SEQUENCE: 29
gtgtttgtaa tggacgattt cttaaagggt att                            33

<210> SEQ ID NO 30
<211> LENGTH: 29
<212> TYPE: DNA
<213> ORGANISM: Artificial
<220> FEATURE:
<223> OTHER INFORMATION: Primer

<400> SEQUENCE: 30
agaccggtac tcctcagcct gctttcgta                                 29

<210> SEQ ID NO 31
<211> LENGTH: 29
<212> TYPE: DNA
<213> ORGANISM: Artificial
<220> FEATURE:
<223> OTHER INFORMATION: Primer
```

```
<400> SEQUENCE: 31
aacggtacca acgctgctgt tcttttca                                29

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
cttggagccg tactggaact                                         20

<210> SEQ ID NO 33
<211> LENGTH: 20
<212> TYPE: DNA
<213> ORGANISM: Artificial
<220> FEATURE:
<223> OTHER INFORMATION: Primer

<400> SEQUENCE: 33
accacagtcc atgccatcac                                         20

<210> SEQ ID NO 34
<211> LENGTH: 20
<212> TYPE: DNA
<213> ORGANISM: Artificial
<220> FEATURE:
<223> OTHER INFORMATION: Primer

<400> SEQUENCE: 34
tccaccaccc tgttgctgta                                         20

<210> SEQ ID NO 35
<211> LENGTH: 29
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (1)..(2), (2)..(3), (3)..(4), (4)..(5), (5)..(6),
      (6)..(7), (7)..(8), (8)..(9), (9)..(10), (10)..(11), (11)..(12),
      (12)..(13), (13)..(14), (14)..(15), (15)..(16), (27)..(28),
      (28)..(29)
<223> OTHER INFORMATION: Phosphorothioate linkage
<220> FEATURE:
<221> NAME/KEY: misc_feature
<222> LOCATION: (1)..(1), (2)..(2), (3)..(3), (14)..(14), (15)..(15),
      (16)..(16)
<223> OTHER INFORMATION: LNA
<220> FEATURE:
<221> NAME/KEY: misc_feature
<222> LOCATION: (28)..(28), (29)..(29)
<223> OTHER INFORMATION: 2-o-Me

<400> SEQUENCE: 35
ctcccaccac atagcagcga uaccaaucg                                29

<210> SEQ ID NO 36
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
```

```
<222> LOCATION: (1)..(2), (2)..(3), (3)..(4), (4)..(5), (5)..(6),
      (6)..(7), (7)..(8), (8)..(9), (9)..(10), (10)..(11), (11)..(12),
      (12)..(13), (13)..(14), (14)..(15), (15)..(16)
<223> OTHER INFORMATION: Phosphorothioate linkage
<220> FEATURE:
<221> NAME/KEY: misc_feature
<222> LOCATION: (1)..(1), (2)..(2), (3)..(3), (14)..(14), (15)..(15),
      (16)..(16)
<223> OTHER INFORMATION: LNA

<400> SEQUENCE: 36
ctcccaccac atagca                                                        16

<210> SEQ ID NO 37
<211> LENGTH: 36
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (21)..(22), (22)..(23), (23)..(24),
      (34)..(35), (35)..(36)
<223> OTHER INFORMATION: Phosphorothioate linkage
<220> FEATURE:
<221> NAME/KEY: misc_feature
<222> LOCATION: (1)..(1), (2)..(2), (3)..(3), (4)..(4), (5)..(5),
      (6)..(6), (7)..(7), (8)..(8), (9)..(9), (10)..(10), (11)..(11),
      (12)..(12), (13)..(13), (14)..(14), (15)..(15), (16)..(16),
      (17)..(17), (18)..(18), (19)..(19), (20)..(20), (21)..(21),
      (22)..(22), (23)..(23), (35)..(35), (36)..(36)
<223> OTHER INFORMATION: 2-o-Me

<400> SEQUENCE: 37
acaaacacca uugucacacu ccaugaauac caaugc                                  36

<210> SEQ ID NO 38
<211> LENGTH: 23
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2), (2)..(3), (21)..(22), (22)..(23)
<223> OTHER INFORMATION: Phosphorothioate linkage
<220> FEATURE:
<221> NAME/KEY: misc_feature
<222> LOCATION: (1)..(1), (2)..(2), (3)..(3), (4)..(4), (5)..(5),
      (6)..(6), (7)..(7), (8)..(8), (9)..(9), (10)..(10), (11)..(11),
      (12)..(12), (13)..(13), (14)..(14), (15)..(15), (16)..(16),
      (17)..(17), (18)..(18), (19)..(19), (20)..(20), (21)..(21),
      (22)..(22), (23)..(23)
<223> OTHER INFORMATION: 2-o-Me

<400> SEQUENCE: 38
acaaacacca uugucacacu cca                                                23

<210> SEQ ID NO 39
<211> LENGTH: 28
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (1)..(2), (2)..(3), (3)..(4), (14)..(15), (15)..(16),
      (16)..(17), (17)..(18), (18)..(19), (19)..(20), (20)..(21),
      (21)..(22), (22)..(23), (23)..(24), (25)..(26), (26)..(27),
      (27)..(28)
<223> OTHER INFORMATION: Phosphorothioate linkage
```

-continued

```
<220> FEATURE:
<221> NAME/KEY: misc_feature
<222> LOCATION: (14)..(14), (16)..(16), (19)..(19), (20)..(20),
      (23)..(23), (25)..(25), (27)..(27), (28)..(28)
<223> OTHER INFORMATION: LNA
<220> FEATURE:
<221> NAME/KEY: misc_feature
<222> LOCATION: (1)..(1), (2)..(2), (3)..(3)
<223> OTHER INFORMATION: 2-o-Me

<400> SEQUENCE: 39
gcgauaccaa ucgccattgt cacactcc                                              28
```